United States Patent [19]

Ramsay Shaw et al.

[11] Patent Number: 5,683,869
[45] Date of Patent: Nov. 4, 1997

[54] METHOD OF NUCLEIC ACID SEQUENCING

[75] Inventors: Barbara Ramsay Shaw; Kenneth W. Porter, both of Durham, N.C.

[73] Assignee: Duke University, Durham, N.C.

[21] Appl. No.: 300,265

[22] Filed: Sep. 2, 1994

Related U.S. Application Data

[63] Continuation-in-part of Ser. No. 115,690, Sep. 3, 1993.
[51] Int. Cl.[6] ............... C12Q 1/68; C07H 21/04; C12P 19/34; C12N 15/00
[52] U.S. Cl. ............... 435/6; 435/91.1; 435/91.2; 536/23.1; 536/24.3; 536/24.33; 536/25.3; 536/25.32; 935/1; 935/76; 935/77; 935/78
[58] Field of Search ............... 435/6, 91.1, 91.2, 435/183; 536/23.1, 24.3, 24.33, 25.3, 25.32; 935/76–78

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,965,188 | 10/1990 | Mullis et al. ............... 435/6 |
| 5,130,302 | 7/1992 | Spielvogel et al. . |
| 5,143,907 | 9/1992 | Spielvogel et al. . |
| 5,177,198 | 1/1993 | Spielvogel et al. . |
| 5,254,706 | 10/1993 | Spielvogel et al. . |
| 5,260,427 | 11/1993 | Spielvogel et al. . |
| 5,354,656 | 10/1994 | Sorge et al. ............... 435/6 |

FOREIGN PATENT DOCUMENTS 9108213  6/1991  WIPO .

OTHER PUBLICATIONS

WPI Acc No.: 87–007206101, Mundy; Abstract only.
Bendayan et al, "Electron Spectroscopic Imaging for High–resolution Immunocytochemistry: Use of Boronated Protein A[1]", The Journal of Histochemistry and Cytochemistry 37(5):573–580 (1989).
Mundy, WO 86/07612 Abstract.

*Primary Examiner*—Bradley L. Sisson
*Attorney, Agent, or Firm*—Nixon & Vanderhye P.C.

[57] ABSTRACT

The present invention relates, in general, to a process of enzymatically synthesizing nucleic acids containing nucleotides that are resistant to degradation. The invention further relates to methods of utilizing such nucleic acids in DNA and RNA amplification and sequencing, gene therapy and molecular detection protocols.

15 Claims, 11 Drawing Sheets

FIG. 1A

ONE-STEP PCR SEQUENCING WITH α-BORONATED dNTP'S

1. ANNEAL LABELED PRIMER 1 AND UNLABELED PRIMER 2 TO DNA TEMPLATE.

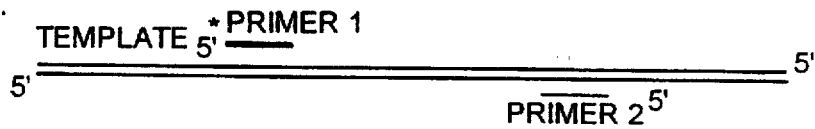

2. IN SEPARATE A-, T-, G-, AND C-SPECIFIC REACTIONS, INCORPORATE THE APPROPRIATE BORONATED 2'-DEOXYNUCLEOTIDE BY PCR AMPLIFICATION. SHOWN HERE ARE EXAMPLES OF THREE SUCH PRODUCTS.

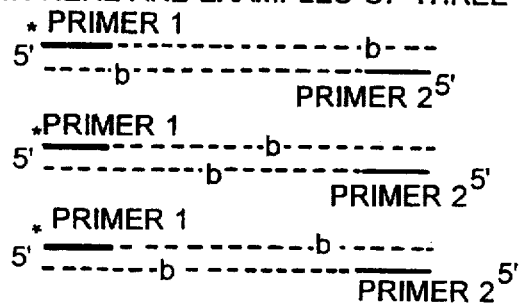

3. DIGEST UP TO THE 3' BORONATED dNMP WITH EXONUCLEASE.

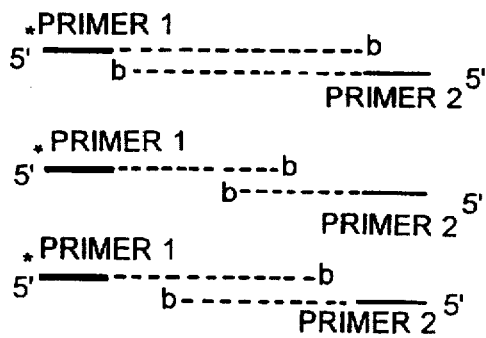

4. SEPARATE FRAGMENTS BY PAGE AND READ THE DNA SEQUENCE.

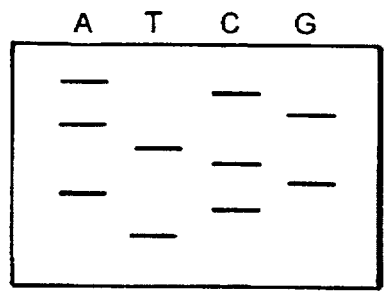

FIG. 1B

BIDIRECTIONAL ONE-STEP SEQUENCING WITH MAGNETIC BEADS

1. ANNEAL BIOTINYLATED PRIMER 1 AND UNMODIFIED PRIMER 2 TO DNA TEMPLATE.

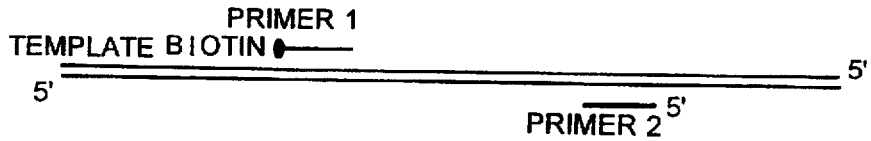

2. IN SEPARATE A-, T-, G-, AND C-SPECIFIC REACTIONS, INCORPORATE BOTH THE APPROPRIATE BORONATED 2'-DEOXYNUCLEOTIDE AND LABEL BY PCR AMPLIFICATION.

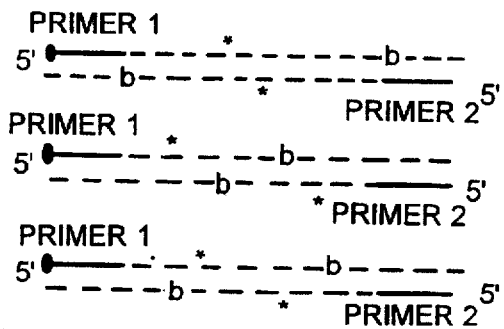

3. BIND BIOTINYLATED PCR PRODUCTS TO STREPTAVIDIN-LINKED MAGNETIC BEADS, IMMOBILIZE BEADS TO MAGNET, WASH WITH BUFFER, AND DIGEST BACK TO THE 3' BORONATED dNMP WITH EXO III.

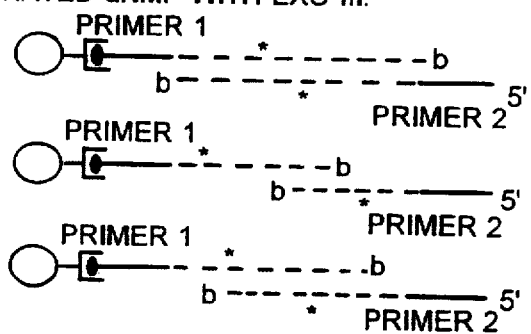

4. UNMODIFIED PRIMER 2 STRAND CAN BE DENATURED IN HOT EXO III BUFFER, THEN BIOTINYLATED PRIMER 1 STRAND CAN BE DETACHED FROM THE BEAD IN HOT LOADING BUFFER. BOTH FRAGMENTS CAN BE SEQUENCED SIMULTANEOUSLY BY PAGE.

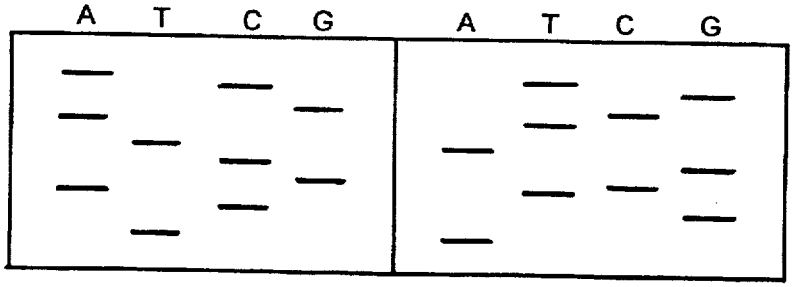

Figure 3 Legend. One-Step PCR Sequencing.

A portion of phage M13mp2 was sequenced by One-Step PCR Sequencing as described in the text. Primer SS20 was labeled and used, along with primer RP, for PCR amplification (250 bp product). Base-specific dNT$^b$Ps were incorporated in four separate reactions and their positions were revealed by digestion with exonuclease III. The digested PCR products were separated by two loadings on a denaturing polyacrylamide gel.

As is shown in the first four lanes of Figure 2, the first loading separated fragments from position $G_{55}$ to about position $A_{210}$. The second loading separated fragments beginning at the first position beyond the 3' end of the primer, position $G_{21}$, to about position $C_{109}$.

On the figure, missing bands are denoted by circled numbers and extra bands are noted in parentheses.

The sequence for M13mp2 extending from position $G_{21}$ is:

| | | | |
|---|---|---|---|
| GTGAGGTCGG | TCGAAAGGCC | GTGGCGAAGA | CCACGGCCTT |
| TGGTCCGTTT | CGCGGTAAGC | GGTAAGTCCG | ATGCGTTGAC |
| AACCCTTCCC | GCTAGCCACG | CCCGGAGAAG | CGATAATGCG |
| GTCGACCGCT | TTCCCCCTAC | ACGACGTTCC | GCTAATTCAA |
| CCCATTGCGG | TCCCAAAAGG | GAAAAGGGTC | |

```
Primer      5'- CAGGAACAGCTATGGCCTC      -3'
Template    3'- GTCCTTGTCGATACCGGAGTCGATGTG -5'
```

METHOD OF NUCLEIC ACID SEQUENCING

This is a continuation-in-part of application Ser. No. 08/115,690, filed Sep. 3, 1993, the entire contents of which is incorporated herein by reference.

This invention was made with Government support under Grant No. HG-00782 awarded by the national Institutes of Health. The Government has certain rights in the invention.

TECHNICAL FIELD

The present invention relates, in general, to a process of enzymatically synthesizing nucleic acids containing nucleotides that are resistant to degradation. The invention further relates to methods of utilizing such nucleic acids in DNA and RNA amplification and sequencing, gene therapy and molecular detection protocols.

BACKGROUND

Cycle sequencing polymerase chain reaction (PCR) products has proven to be an effective alternative to the more traditional M13 sequencing technique. Advantages include the use of thermostable polymerases that allow high annealing and extension temperatures (Gyllenstein and Erlich, *Proc. Natl. Acad. Sci. USA* 85:7652 (1988), Innis et al, *Proc. Natl. Acad. Sci. USA* 85:9436 (1988)), as well as the ability to directly utilize double-stranded DNA for templates (Carothers et al, *Biotechniques* 7:494; Sears et al, *Biotechniques* 13:626 (1992)). High temperature annealing and extension reduce ambiguous sequencing data that arise because of mispriming and/or secondary structure of the template. The capability of sequencing double-stranded DNA allows PCR products to be sequenced immediately after amplification. However, a simpler method for sequencing PCR products is to incorporate sequence delimiters directly into the PCR amplification process.

A sequencing method based on the incorporation of 5'-α-thiotriphosphates into PCR products has been demonstrated (Nakamaye et al, *Nucl. Acids Res.* 16:9947 (1988)). 5'-α-Thiotriphosphates were incorporated into DNA during PCR amplification and the positions of incorporated base-specific 5'-α-thiotriphosphates were revealed by chemical degradation with either 2-iodoethanol or 2,3-epoxy-1-propanol. Also 5'-α-thiotriphosphates have been used to sequence single stranded M13 DNA (Labeit et al, *Meth. Enzymol.* 155:166 (1987)). After incorporation by Klenow into primer extension products, the positions of the 5'-α-thiotriphosphates were revealed by exonuclease III digestion. However, attempts to combine the best features of both methods (PCR amplification and enzymatic digestion) to reveal the sequence delimiters have proven unsatisfactory because of uneven band intensity (Nakamaye et al, *Nucl. Acids Res.* 16:9947 (1988); Olsen and Eckstein, *Nucl. Acids Res.* 17:9613 (1989)). The present invention overcomes the problems of the art and provides a simple and accurate method of amplifying and sequencing nucleic acids in a single step. Furthermore, the method is fast and amenable to automation.

OBJECTS AND SUMMARY OF THE INVENTION

It is a general object of the invention to provide a method of enzymatically incorporating into a nucleic acid a modified nucleotide which, once incorporated, is stable to chemical or enzymatic degradation. It is a specific object of the invention to provide methods of nucleic acid amplification, including strand displacement amplification, nucleic acid sequencing, in vitro transcription and gene therapy. It is a further object of the invention to provide methods of probing molecular interactions of nucleic acids with other cellular components, which methods are based on the enzymatic incorporation into the nucleic acids of modified nucleotides, particularly, α-boronated deoxynucleoside triphosphates.

In one embodiment, the present invention relates to a method of synthesizing a nucleic acid fragment comprising:

contacting a nucleic acid template with:
  i) a primer sufficiently complementary to a portion of the template to hybridize therewith,
  ii) an enzyme that extends the primer so that a product complementary to the template is produced, and
  iii) four different nucleotides at least one of which, once incorporated into the nucleic acid, is resistant to enzymatic degradation, the contacting being effected under conditions such that the at least one nucleotide is recognized by the enzyme and is thereby incorporated into the extension product of the primer.

In another embodiment, the present invention relates to a method of sequencing a nucleic acid comprising:

i) enzymatically amplifying the nucleic acid in the presence of (a) four nucleotides that, once incorporated into a product of the amplification, are susceptible to enzymatic degradation, and (b) a first modified nucleotide that is selectively incorporated into the product of the amplification in lieu of a first of the four nucleotides of (a), which first modified nucleotide, once incorporated into the product of the amplification is resistant to enzymatic degradation, and repeating the enzymatic amplification in the presence of a second, third and fourth modified nucleotide, each of which second, third and fourth modified nucleotides is selectively incorporated into the product of the amplification in lieu of a second, third and fourth of the nucleotides of (a), each of the second, third and fourth modified nucleotides being resistant to enzymatic degradation once incorporated into the product of the amplification;

ii) treating the products of the amplification of step (i) containing the first, second, third and fourth modified nucleotides with an enzyme that digests the products in the 3' to 5' direction, the digestions terminating at the sites of incorporation of the modified nucleotides;

iii) separating the fragments resulting from the treatment of step (ii) and detecting the position of each of the modified nucleotides in the products of the amplification.

In a further embodiment, the present invention relates to a method of sequencing a nucleic acid comprising:

i) enzymatically amplifying the nucleic acid in the presence of (a) four nucleotides that, once incorporated into a product of the amplification, are susceptible to enzymatic degradation, and (b) a first modified nucleotide that is selectively incorporated into the product of the amplification in lieu of a first of the four nucleotides of (a), which first modified nucleotide, once incorporated into the product of the amplification is resistant to enzymatic degradation, and repeating the enzymatic amplification in the presence of a second, third and fourth modified nucleotide, each of which second, third and fourth modified nucleotides is selectively incorporated into the product of the amplification in lieu of a second, third and fourth of the nucleotides of (a), each of the second, third and fourth modified nucleotides being resistant to enzymatic degradation once incorporated into the product of the amplification;

ii) subjecting the products of the amplification of step (i) containing a first, second, third and fourth modified nucleotides to mass spectrometry and detecting the resulting fragment patterns and thereby the position of each of the modified nucleotides in the products of the amplification.

In yet another embodiment, the present invention relates to a method of producing a protein comprising introducing into a cell a nucleic acid sequence encoding the protein, which nucleic acid sequence includes a modified nucleotide that is resistant to enzymatic degradation, the introduction being effected under conditions such that the nucleic acid sequence is expressed and the protein thereby produced.

In yet another embodiment, the present invention relates to a method of amplifying a DNA sequence comprising:

i) contacting the DNA sequence with a primer having a first part and a second part, the first part having a nucleotide sequence such that the first part hybridizes to a portion of the DNA sequence, and the second part being 5' to the first part, noncomplementary to the DNA sequence and having a nucleotide sequence that includes a restriction enzyme recognition site, wherein the contacting is effected under conditions such that the first part of the primer hybridizes to the DNA sequence; and ii) enzymatically extending the primer and the DNA sequence in the presence of a boronated deoxynucleoside triphosphate so that a boronated duplex extension product is produced, the boronated deoxynucleoside triphosphate being selected so that a boronated deoxynucleoside is inserted into the extended DNA sequence at the site of cleavage of the restriction enzyme;

iii) contacting the duplex extension product with the restriction enzyme under conditions such that the second part of the primer is nicked; and iv) Contacting the nicked duplex extension product resulting form step (iii) with a polymerase that effects strand displacement under conditions such that a nucleic acid is produced from the site of the nick that is complementary to the extended DNA sequence.

Further objects and advantages of the present invention will be clear from the description that follows.

BRIEF DESCRIPTION OF THE DRAWINGS

FIG. 1. One step PCR sequencing with α-boronated deoxynucleoside triphosphates (dNT$^b$P's) (FIG. 1A). Bidirectional one-step sequencing with magnetic beads (FIG. 1B).

FIG. 3. The sequence for M13mp2 extending from position $G_{21}$(SEQ ID NO: 14).

Figure 2:
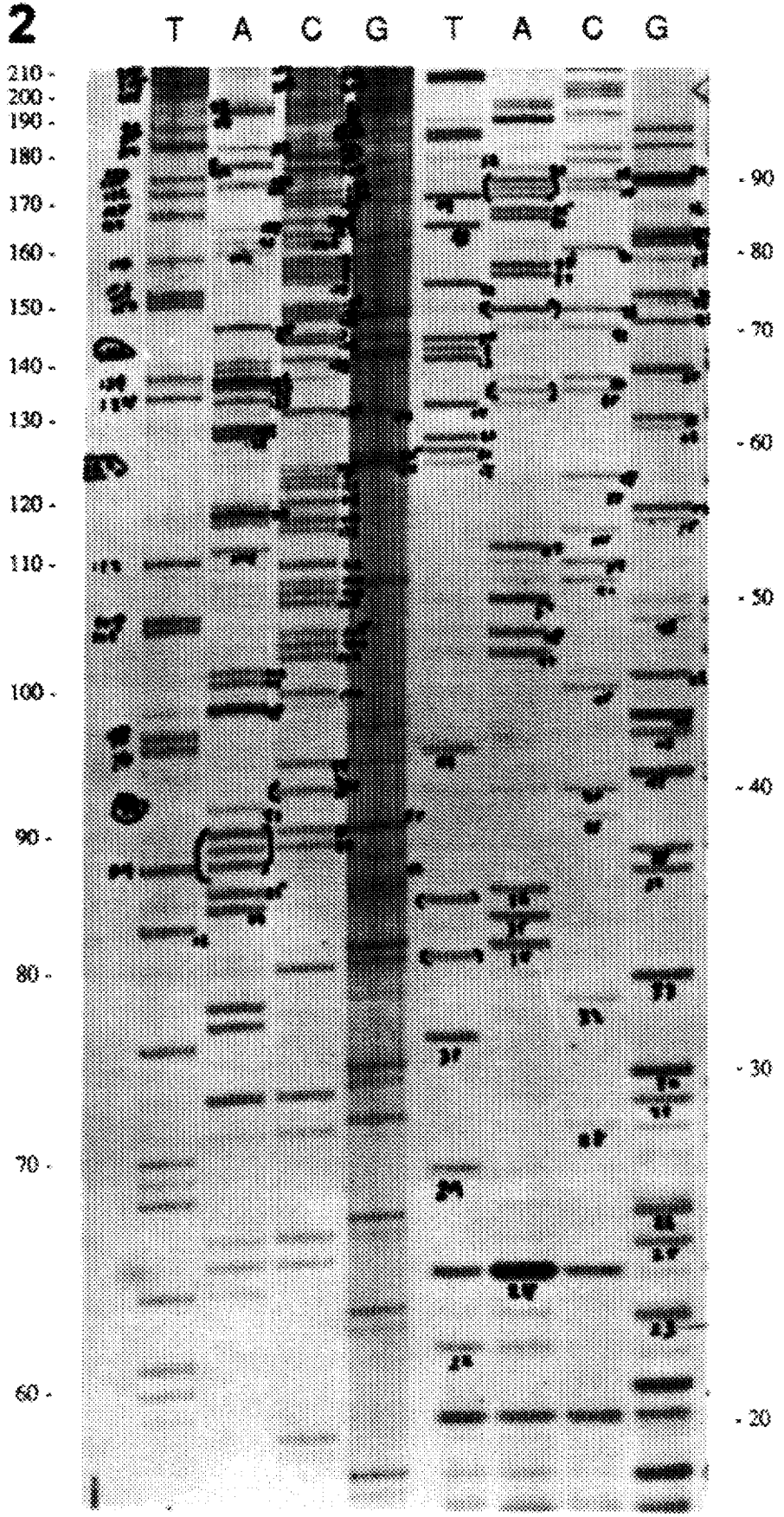
FIG. 2. A portion of M13mp2 sequenced by the one-step process described in FIG. 1A. Primer SS20 was labeled and used, along with primer RP, for PCR amplification (250 bp product). Base-specific dNT$^b$P's were incorporated in four separate reactions and their positions were revealed by digestion with exonuclease III. The digested PCR products were separated by two loadings on a denaturing polyacrylamide gel. As is shown in the first four lanes, the first loading separated fragments from position $G_{55}$ to about position $A_{210}$. The second loading separated fragments beginning at the first position beyond the 3' end of the primer, position $G_{21}$, to about position $C_{109}$. Missing bands are denoted by circled numbers and extra bands are noted in parentheses.

PCR. PCR was performed in the presence of: all normal dNTPs, lane 1; normal dNTPs+2% dAT$^b$P, lane 3; normal dNTPs+2% dTT$^b$P, lane 5; normal dNTPs+2% dGT$^b$P, lane 7; and normal dNTPs+4% dCT$^b$P, lane 9.

Exonuclease. An aliquot of each PCR reaction was digested with exonuclease III: all normal dNTPs, lane 2; normal dNTPs+2% dAT$^b$P, lane 4; normal dNTPs+2% dTT$^b$P, lane 6; normal dNTPs+2% dGT$^b$P, lane 8; and normal dNTPs+4% dCT$^b$P, lane 10. DNA marker is in lanes labeled "M".

Figure 5:
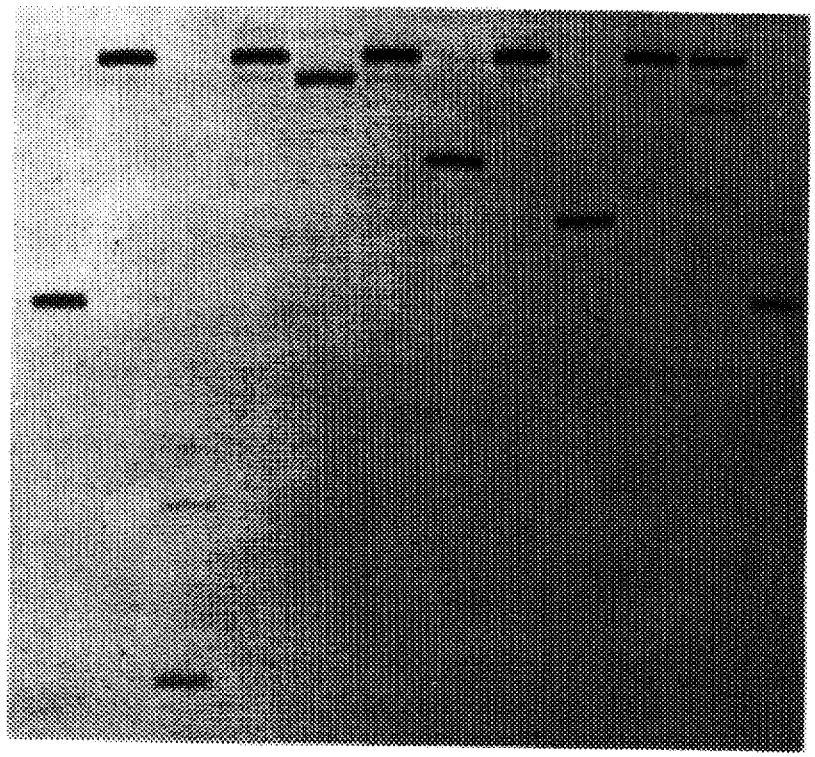

FIG. 5. Primer extension/exonuclease III digestion with dNT$^b$Ps.

Extension. The primer (unextended, lanes labeled P) was extended to the full length of the corresponding template in all instances: all normal dNTPs, lane 1; dAT$^b$P+normal dT-, dG-, dCTP, lane 3; dTT$^b$P+normal dA-, dG-, dCTP, lane 5; dGT$^b$P+normal dA-, dT-, dCTP, lane 7; and dCT$^b$P+normal dA-, dT-, dGTP, lane 9.

Exonuclease. Following extension, an aliquot of each sample was digested with exonuclease III. The all-normal product was digested to the limit of a duplex substrate, lane 2 (exonuclease III requires double-stranded substrate). In each case in which a boronated deoxynucleotide was substituted for a normal, exonuclease digestion was halted at the position of the boronated substitution: at A, lane 4; at T, lane 6; at G, lane 8; and at C, lane 10.

Figure 6A:
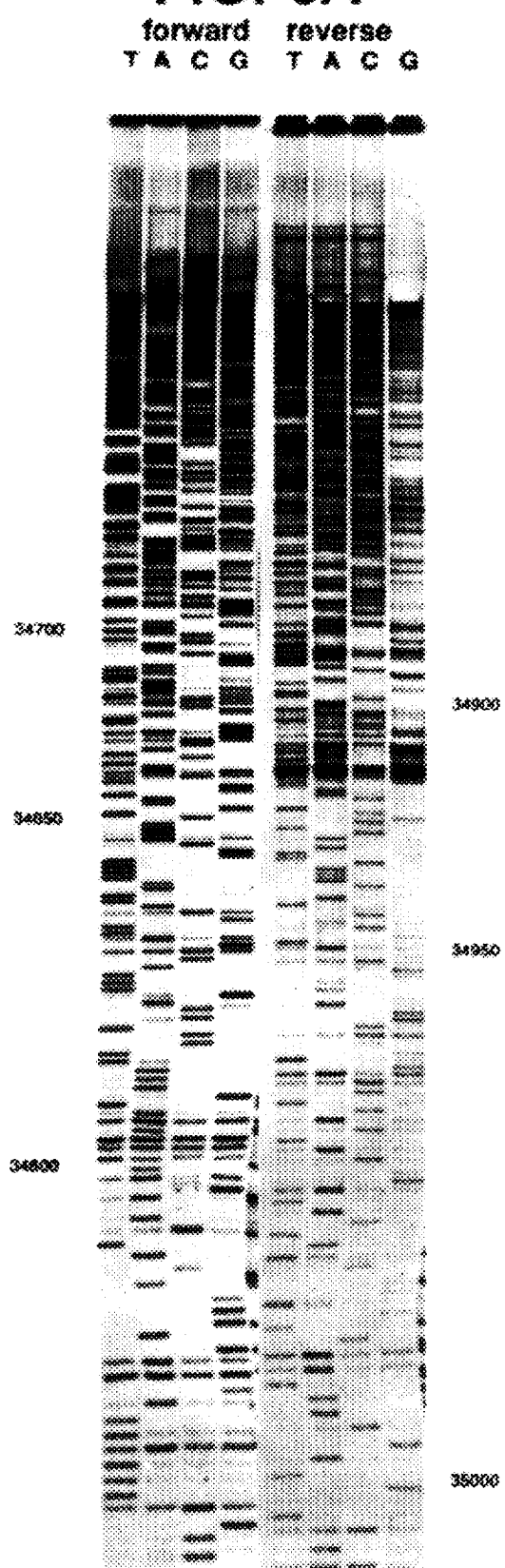
Figure 6B:
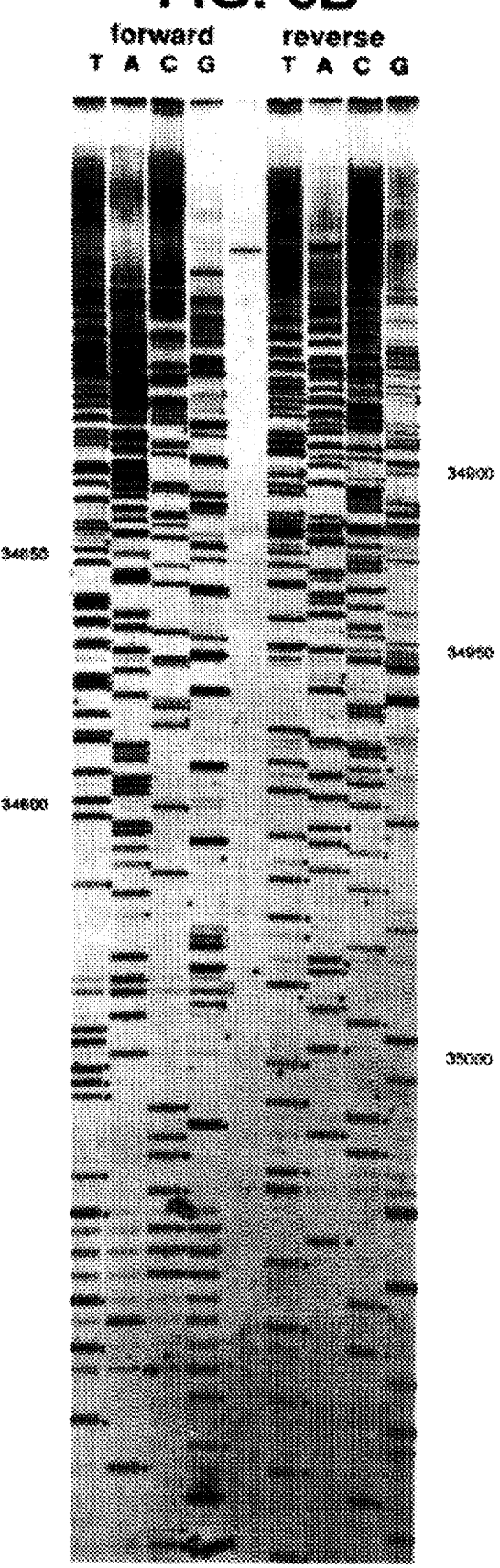

FIG. 6. One-step PCR sequencing with end-labeled primer. FIG. 6A. Both strands of a portion of phage T7 were sequenced. The top strand was sequenced by labeling primer T7$_{rev}$, likewise the bottom strand was sequenced by labelling primer T7$_{for}$. In each case, PCR amplification was accomplished with one labeled and one unlabeled primer (509 bp product). Base-specific dNT$^b$Ps were incorporated in four separate reactions and their positions were revealed by digestion with exonuclease III. The forward sequence could be determined from $C_{34586}$ to $G_{34916}$; the reverse sequence could be determined from $A_{34660}$ to $G_{35000}$ (second loading not shown). Therefore, both strands were sequenced over approximately 350 bases. FIG. 6B. One-step sequencing was repeated for the T7 samples as described for FIG. 6A except that the amount of exonuclease III was increased from 25 units to 130 units. The sequence for phage T7 extending from position 34534 to 35042 is:

```
                                    GGAGCG TAGGAAATAA
TACGACTCAC TATAGGGAGA GGCGAAATAA TCTTCTCCCT GTAGTCTCTT    600
AGATTTACTT TAAGGAGGTC AAATGGCTAA CGTAATTAAA ACCGTTTGA
CTTACCAGTT AGATGGCTCC AATCGTGATT TTAATATCCC GTTTGAGTAT    700
```

-continued

```
CTAGCCCGTA AGTTCGTAGT GGTAACTCTT ATTGGTGTAG ACCGAAAGGT

CCTTACGATT AATACAGACT ATCGCTTTGC TACACGTACT ACTATCTCTC   800

TGACAAAGGC TTGGGGTCCA GCCGATGGCT ACACGACCAT CGAGTTACGT

CGAGTAACCT CCACTACCGA CCGATTGGTT GACTTTACGG ATGGTTCAAT   900

CCTCCGCGCG TATGACCTTA ACGTCGCTCA GATTCAAACG ATGCACGTAG

CGGAAGAGGC CCGTGACCTC ACTACGGATA CTATCGGTGT CAATAACGAT  1000

GGTCACTTGG ATGCTCGTGG TCGTCGAATT GTGAACCTAGS CGA(SEQ ID NO:1)
```

Figure 7A:
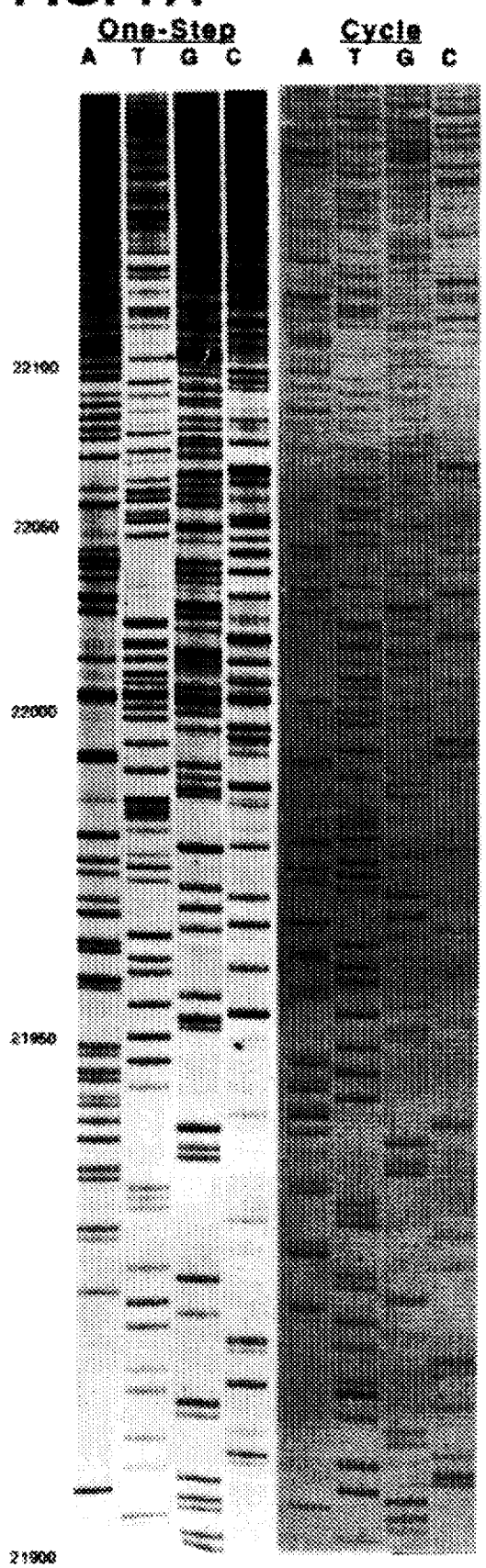
Figure 7B:
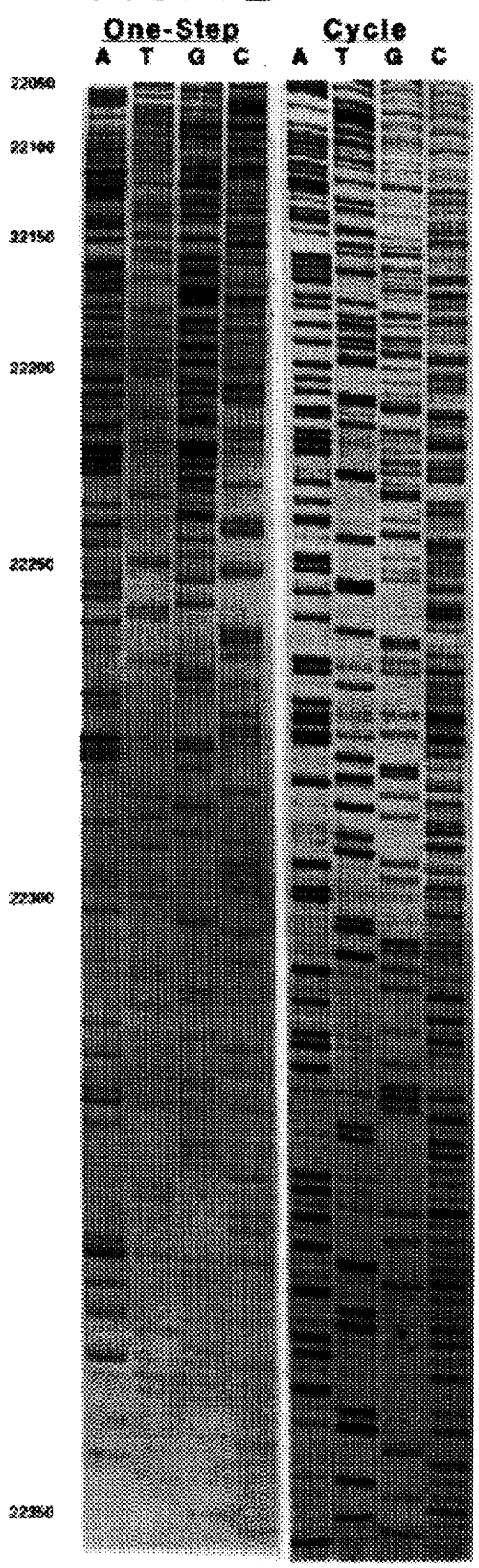

FIG. 7. Bi-directional one-step PCR sequencing with a biotinylated primer. Both strands of a portion of phage T7 were sequenced. The top strand was sequenced using primer phi9$_{rev}$; likewise the bottom strand was sequenced using primer phi9$_{for}$ which was biotinylated prior to PCR amplification. Base-specific dNT$^b$Ps were incorporated in four separate PCR reactions (629 bp product) and their positions were revealed by digestion with exonuclease III. The forward sequence could be determined from T$_{21900}$ to A$_{22100}$; the reverse sequence could be determined from G$_{22350}$ to G$_{22050}$. Therefore, both strands were sequenced for 200-300 bases from a single loading. For comparison, cycle sequencing (right lanes) was performed with labeled primers according to the manufacturer's instructions (Perkin Elmer). The sequence for phage T7 extending from position 21786 to 22414 is:

onated dGTP+dCTP+dATP (lane 9). The amplification was performed for 25 cycles of 95° C. for 1', 53° C. for 1', and 76° C. for 1'.

Lower panel: In vitro transcription. The reaction mixture (55 µl total) contained DNA from the PCR reactions (10 µl ), translation buffer (final concentrations: 40 mM Tris-HCl (pH 8.1), 20 mM MgCl$_2$, 1 mM spermidine, 5 mM DTT, 5 µg/mL BSA, and 0.01% Triton X-100; 11.3 µl), RNasin (USB, 3 µl ), T7 RNA polymerase (80 units), and NTPs (2 mM each). The reaction was carried out for 2 hours at 37° C. The substitution pattern of boronated templates corresponds to that described for the upper panel, ie all normal (lane 2), boronated dGTP (lane 3), boronated dCTP (lane 4), boronated dATP (lane 5), boronated dGTP+dCTP (lane 6), boronated dGTP+dATP (lane 7), boronated dCTP+dATP (lane 8), and boronated dGTP+dCTP+dATP (lane 9).

```
                                     ACAG CTTCACCTGA  800

GGCTATGGCT GCTGCCGCTG ATTCCGTAGG TTTACAGCCG GGAATTTATT

ACGACTCACT ATAGGGAGAC CTCATCTTTG AAATGAGCGA TGACAAGAGG   900

TTGGAGTCCT CGGTCTTCCT GTAGTTCAAC TTTAAGGAGA CAATAATAAT

GGCTGAATCT AATGCAGACG TATATGCATC TTTTGGCGTG AACTCCGCTG  1000

TGATGTCTGG TGGTTCCGTT GAGGAACATG AGCAGAACAT GCTGGCTCTT

GATGTTGCTG CCCGTGATGG CGATGATGCA ATCGAGTTAG CGTCAGACGA  1100

AGTGGAAACA GAACGTGACC TGTATGACAA CTCTGACCCG TTCGGTCAAG

AGGATGACGA AGGCCGCATT CAGGTTCGTA TCGGTGATGG CTCTGAGCCG  1200

ACCGATGTGG ACACTGGAGA AGAAGGCGTT GAGGGCACCG AAGGTTCCGA

AGAGTTTACC CCACTGGGCG AGACTCCAGA AGAACTGGTA GCTGCCTCTG  1300

AGCAACTTGG TGAGCACGAA GAGGGCTTCC AAGAGATGAT TAACATTGCT

GCTGAGCGTG GCATGAGTGT CGAGACCATT GAGGCTATCC AGCGTGAGTA  1400

CGAGGAGAAC GAAGA(SEQ ID NO:2)
```

Figure 8:
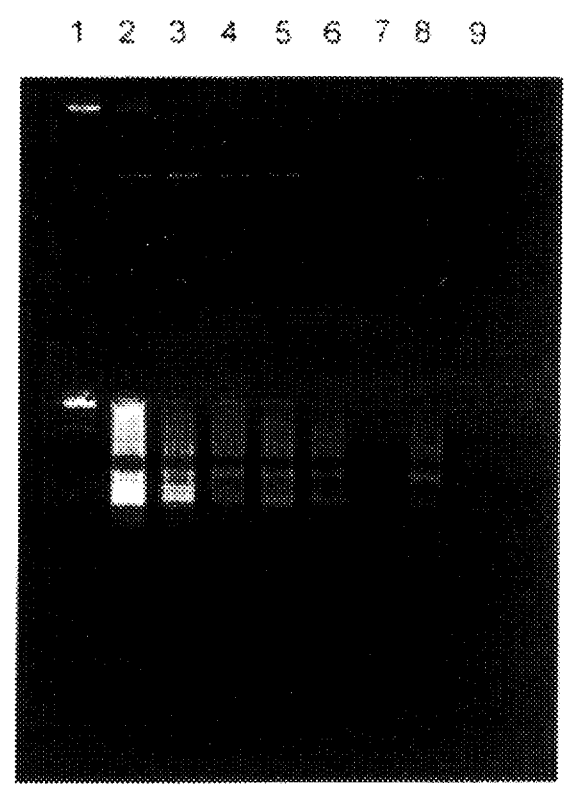

FIG. 8. PCR amplification using boronated dNTPs and in vitro transcription of boronated templates.

Upper panel. PCR amplification. The reaction mixture (50 µl total) contained T7 DNA (10 µg), forward primer (T7 positions 34534-34553; 10 pmol), reverse primer (complementary to T7 positions 34625-4644), PCR buffer, Vent DNA polymerase (New England Biolabs, 1 unit), and dNTPs (200 µM) which were the normal triphosphates except that boronated triphosphates were substituted for the normal one(s) as follows: all normal (lane 2), boronated dGTP (lane 3), boronated dCTP (lane 4), boronated dATP (lane 5), boronated dGTP+dCTP (lane 6), boronated dGTP+dATP (lane 7), boronated dCTP+dATP (lane 8), and bor- Electrophoresis. All samples were mixed with a sucrose loading buffer, separated on a 5% agarose gel, and visualized by ethidium bromide fluorescence. Lane 1 of each panel contains marker DNA.

Figure 9A:
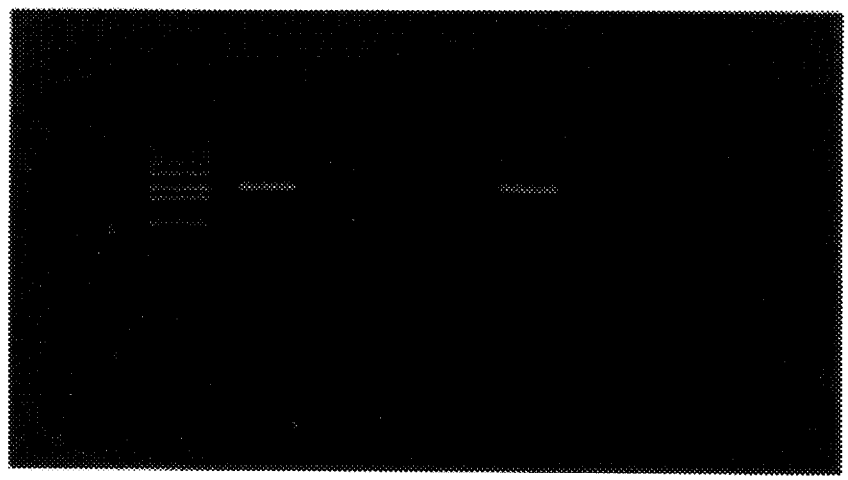
Figure 9B:
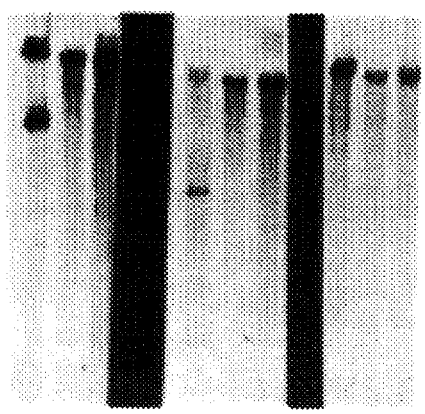
Figure 9C:

FIG. 9. Incorporation of boronated dNTPs into DNA by PCR; resistance of boronated DNA to mouse serum and exonuclease digestion; transcription of boronated DNA into mRNA; and translation of mRNA into protein. FIG. 9A. Mouse serum digestion of normal (lane 1) and resistant boronated (lane 4) PCR products. FIG. 9B. Production of PCR products—normal (lane 1), boronated (lanes 2 and 3); exonuclease III digested normal PCR products (lane 4) and resistant boronated PCR product (lanes 5 and 6); transcription of normal and boronated DNA (lanes 7-9). FIG. 9C.

Translation of normal (lane 1) and boronated (lane 2 dG^b, lane 3 dC^b) PCR products.

Figure 10:
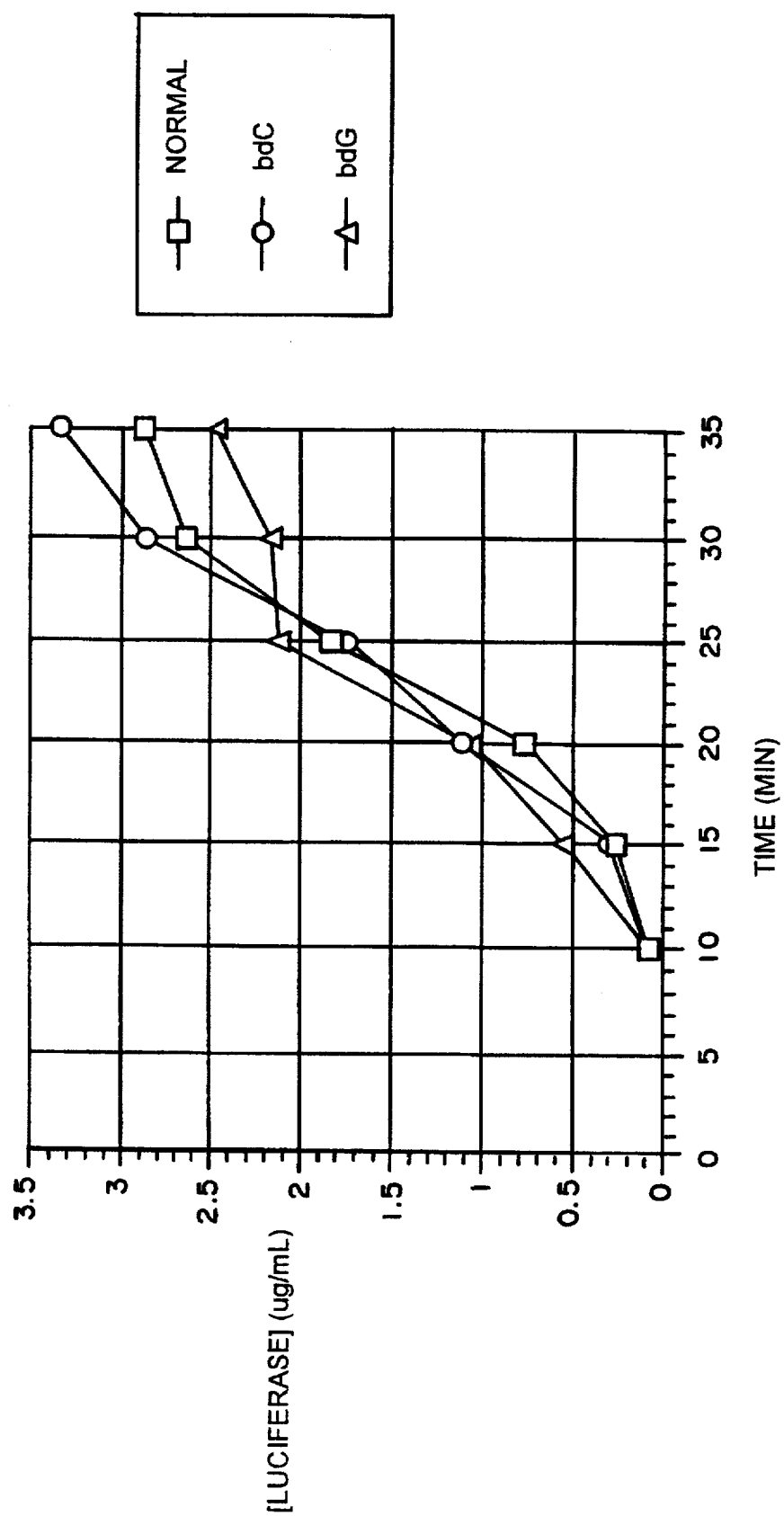

FIG. 10. Expression of normal and boronated templates.

Figure 11:
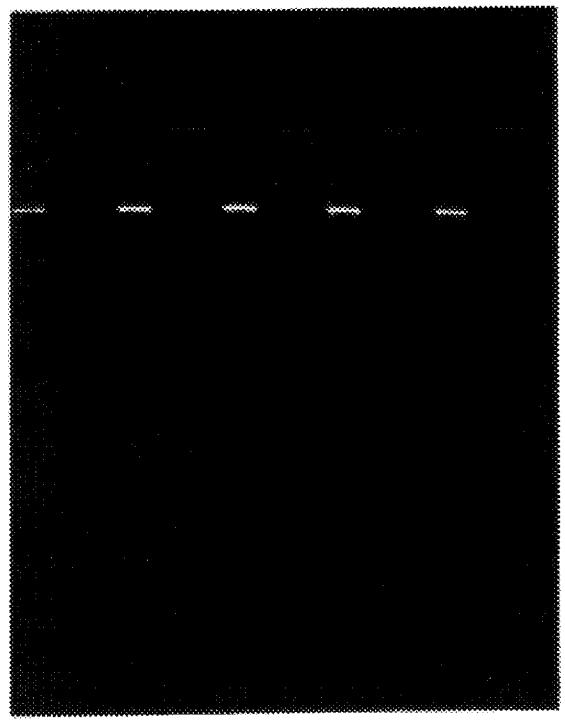

FIG. 11. Resistance to 5' exonuclease digestion by boronated PCR products. Lane 1—all normal, lane 2—all normal/exo, lane 3—dAT^bP, lane 4—dAT^bP/exo, lane 5—dTT^bP, lane 6—dTT^bP/exo, lane 7—dGT^bP, lane 8—dGT^bP/exo, lane 9—dC^bP, lane 10—dCT^bP/exo. Note: The exo+ samples (lanes 2, 4, 6, 8, 10) appear to migrate more slowly than the exo− samples (lanes 1, 3, 5, 7, 9) because they were loaded at different times. The size of the fragments is the same.

DETAILED DESCRIPTION OF THE INVENTION

The present invention results, at least in part, from the discoveries that deoxynucleoside borano-phosphates can be enzymatically incorporated into nucleic acids and that once incorporated, such nucleotides are stable to enzymatic (eg exonuclease) digestion. These discoveries make possible unique approaches to nucleic acid amplification and sequencing, DNA structure determination and therapeutics, including antisense and gene therapy. The present invention relates to these approaches, as well as to others.

In one embodiment, the present invention relates to a method of simultaneously amplifying a nucleic acid (eg, by PCR for DNA or by reverse transcriptase type reaction for RNA) and sequencing the product obtained. The method involves the utilization of modified nucleotides that can be enzymatically incorporated into nucleic acids in lieu of their unmodified, naturally occurring counterparts. The modified nucleotides are, preferably, nucleoside boranotriphosphates, eg, 5'-α-borano-triphosphates:

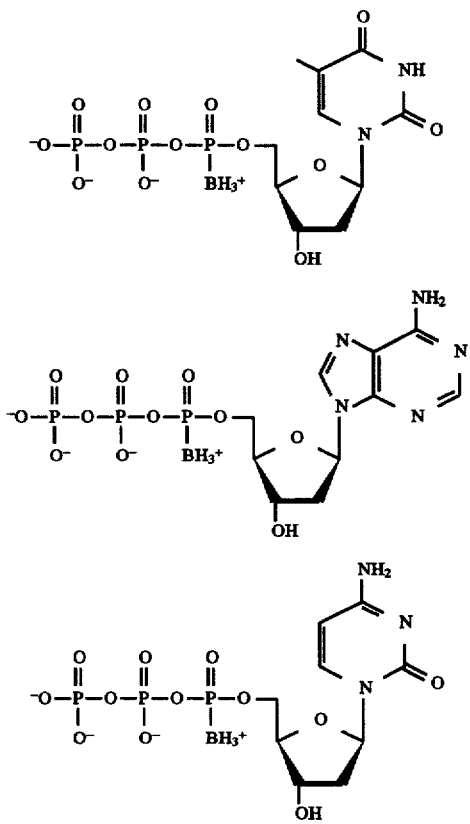

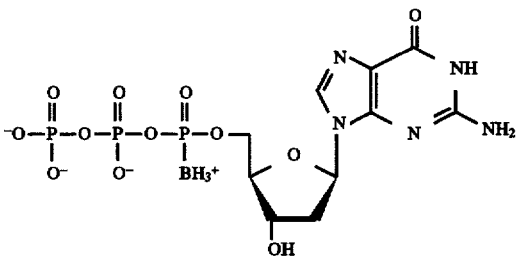

The borano moiety can be —BH₃ (as indicated above), or other such moiety as described in U.S. Pat. No. 5,177,198. The Examples set forth herein relate to boronated compounds, however, it will be appreciated that other elements having a large neutron capture cross-section for low energy neutrons, and suitable for use in neutron capture therapy, such as gallium, can also be used. The base moiety of modified nucleotides suitable for use in the present invention can be a naturally occurring base or a derivative, such as 7-deaza-guanine, inosine, 5-methylcytosine, etc (see U.S. Pat. No. 5,177,198). The use of modified bases can be advantageous for reasons noted in Current Protocols in Molecular Biology, pp. 7.0.1–7.7.31, eds. Ausubel et al, Greene Publishing Associates, Inc. and John Wiley & Sons, Inc. (1993). One skilled in the art will appreciate that it may also be advantageous to utilize modified sugar moieties.

The base-specific incorporation of modified nucleotides (eg, 2'-deoxynucleoside5'-borano-triphosphates) into DNA can be effected during primer extension using protocols such as PCR (described in U.S. Pat. Nos. 4,683,195 and 4,683, 202). Other enzymatic protocols can also be used, such as those employing diphosphates rather than triphosphates as substrates. The optimum polymerase incorporates dNT^bPs efficiently, base-specifically and independent of the surrounding sequence context. Taq polymerase and Vent polymerase can be used, as can other thermostable polymerases. When RNA sequencing is sought, Tth polymerase can be used. Once incorporated, the modified nucleotides block the action of exonucleases, for example, exonuclease III, or other 3'→5' exonuclease that cleaves normal phosphodiesters but to which the modified nucleotide (eg, boranophosphate) proves resistant, thereby making it possible to determine the position of the 3' borano-phosphate in each amplification product.

As an alternative to the exonuclease treatment described above, one skilled in the art will appreciate that techniques such as mass spectrometry can also be used to detect the location of the modified nucleotide. It has been shown that DNA can be sequenced by Matrix-Assisted Laser Desorption/Ionization Mass Spectrometry (MALDI-MS; Tang et al, Rapid Comm. in Mass. Spectrom. 7:63 (1993); Wu et al, Rapid Comm. in Mass. Spectrom. 7:142 (1993)). The procedure involves using mass spectrometry, which can be accomplished in minutes, to analyze sequencing reactions. With MALDI-MS, it has been possible to determine the sequence for about 40 nucleotides of standard base-specific sequencing reactions. Boron is found only in trace amounts in DNA or RNA and it has several natural isotopes. Therefore it is a good biomarker for mass spectrometry. Since boronated triphosphates can be incorporated base-specifically in sequencing reactions, it should be possible to attach a boron tag to the sequencing reaction products to aid in the separation and identification of the molecular fragments by MALDI-MS.

The method of the present invention, as it relates to one-step PCR sequencing using α boronated dNTP's, is depicted in FIG. 1A. As shown in FIG. 1A, the method can be carried out in four simple manipulations in a "one-pot" reaction:

1. Primer labeling: One of two PCR primers, specific for the region to be amplified, is labeled at the 5' end with a detectable label, for example, a radioactive, fluorescent or chemiluminescent label. If both strands are to be sequenced, uniquely labeled primers for both strands must be provided. (Alternatively (if bi-directional amplification is not required), the modified nucleotide to be incorporated can be labeled rather than the primer. The label can be on the base moiety, sugar moiety, or on the boron moiety of the modified nucleotide. In addition to radioactive, fluorescent and chemiluminescent labels, binding pair members can also be used, such as biotin, as can other labels known in the art. Antibodies directed to moieties of the modified nucleotide can also be used for purposes of detection.)

2. Base-specific reactions: Four separate PCR amplifications are performed in the presence of the four normal dNTP's (dA, dT, dG and dC), plus one of the $dNT^bP$'s, preferably, present at a low level (eg, for dA, 10:1 normal to boronated; for dT, 5:1, normal to boronated; for dG, 10:1 normal to boronated; for dC, 1:2 normal to boronated). (Alternatively, the amplifications can be performed simultaneously using four polymerases selected so as to be specific for only one of the boronated dNTP's.)

3. Exonuclease digestion: Each of the base-specific PCR reaction products is digested with 3' to 5' exonuclease, for example, exonuclease III, to produce fragments that terminate at base-specific $dNM^bPs$. (Alternatively, fragmentation can be effected, as well as detection, using the spectrometric method described above.)

4. Fragment separation: Upon separation (eg, by electrophoresis), the borano-terminated fragments produce a uniform band pattern marking the position of each base in the PCR product.

The above-described process is advantageous as it is direct—the primers can be pre-labeled and the sequence delimiters (eg, the boranophosphates) can be incorporated during amplification. Therefore, the present method eliminates the need to remove unextended primers and truncated extension products from the PCR products in preparation for sequencing. Further, the nucleic acid purification and the secondary cycle sequencing procedure can be replaced by a simple and completely automatable exonuclease digestion that reveals the chain truncators (the modified nucleotides). The one-step solution to cycle sequencing afforded by the present method reduces the time substantially between initiation of amplification and separation of the fragments obtained (it should be noted, however, that boranocontaining compounds can also be used as truncators in a cycle sequencing approach). Just as important as the time savings is the elimination of the nucleic acid purification step which renders the technique amenable to automation, as described below.

In addition to the protocol depicted in FIG. 1A, the present method can also be used to effect bidirectional sequencing. An exemplary approach utilizing magnetic beads is set forth in FIG. 1B and is described below. Magnetic bead technology has been demonstrated to be an effective method for the dideoxy sequencing of PCR products (Hultman et al, Nucl. Acids Res. 17:4937 (1989), Biotechniques 10:84 (1991)). In the context of the present method, magnetic beads can: (1) facilitate exonuclease digestion of the PCR products and (2) allow both strands of the PCR template to be sequenced. First, one of the primers is modified with a first member of a binding pair, for example, biotin and then a label and boronated nucleotides are incorporated during amplification. Following amplification, the duplex DNA is immobilized to magentic beads linked to the other member of the binding pair (eg when biotin is the first member of the binding pair, streptavidin-linked magnetic beads can be used) and treated with exonuclease. Following digestion, the fragments from each strand are isolated independently and separated, for example, by PAGE to produce the sequence. The procedure shown in FIG. 1B is outlined below.

1. Perform four base-specific dA, dT, dG, and dC reactions: Four separate PCR amplifications are performed with one biotinylated and one unmodified primer in the presence of all four normal dNTPs plus a few percent of one of the $dNT^bPs$ (eg, for dA, 10:1 normal to boronated; for dT, 5:1, normal to boronated; for dG, 10:1 normal to boronated; for dC, 1:2 normal to boronated). Also, sufficient labelled dNTP (radioactive or other) is added to the reaction such that the boronated chain delimiter (and label, if appropriate) is incorporated during PCR amplification.

2. Bind the PCR products to streptavidin-linked magnetic beads. The biotinylated PCR products are incubated with streptavidin-linked magnetic beads and then the PCR product-biotin-streptavidin-magnetic bead complexes can be immobilized with a magnet. While the complexes are immobilized, they can be washed to remove PCR reactants and the buffer changed to the optimal exonuclease buffer.

3. Digest with exonuclease III. While still attached to the magnetic beads, each of the base-specific PCR reaction products is digested with exonuclease III to produce fragments which terminate at base-specific $dNM^bPs$.

4. Remove the unmodified primer strand. Digested fragments derived from the unmodified (eg, non-biotinylated) primer strand are separated from the biotinylated strand, for example, by heating the digestion reaction mixture. The biotinylated strand fragments are immobilized with the magnet and the unmodified fragments are removed in the exonuclease buffer and loaded onto the sequencing gel.

5. Remove the biotinylated strand from the magnetic beads. Digested fragments derived from the biotinylated primer can be removed from the streptavidin-linked magnetic beads, for example, by heating the complexes in loading buffer (see Tong et al, Anal. Chem. 64:2672 (1992)). The free magnetic beads are immobilized with the magnet and the biotinylated fragments are removed in loading buffer and loaded directly onto the sequencing gel.

While the foregoing is described by way of reference to a biotin/avidin binding pair, alternative binding pairs can also be used.

In addition to the approaches described in FIGS. 1A and 1B, the present invention relates to a method of "mirror-image" sequencing. In this method, 5' and 3' exonucleases are used in concert to produce mirror image sequence data derived from each strand of duplex DNA. For example, a duplex PCR product is digested from the same end by using a 5' exonuclease, such as T7 gene 6 or λ exonuclease, for the Watson strand, and a 3' exonuclease for the Crick strand. In each case, digestion proceeds until the nuclease encounters a base-specific boronated nucleotide, at which point digestion is blocked, thereby producing a family of sequencing fragments. Since the fragments derived from the two complementary strands are digested from the same end, the length of the fragments at each position in the sequence will be the same. Therefore the sequencing gel will produce side-by-side mirror images of the sequence, thus providing immediate and independent sequence verification.

"Mirror-image" sequencing involves the use of a 5'-exonuclease that shows differential digestion towards normal and borano-phosphates. The degree of susceptibility of the borano-phosphates to an exonuclease can be determined experimentally. Using an appropriate pair of nucleases and borano-stereoisomers, the experiment is performed as follows: (a) following PCR, the labeled products are split into separate tubes and digested with a double-strand specific 5' or 3' exonuclease, generating two sequencing ladders, one each from the Watson and Crick strands; or (b) one biotinylated primer is used and the label and boranophosphates are incorporated during PCR. The strands are then separated into two vessels where the 5' and 3' exonuclease digestions are performed. Nucleases here must be single-strand specific, such as exonuclease I (3') and phosphodiesterase II (5').

The potential uses for the sequencing procedures described herein will be clear to those skilled in the art. For example:

(i) The shotgun method of large scale sequencing relies on breaking up cosmid-sized DNA into smaller pieces that are cloned into phage M13. The ssM13 templates are then sequenced with universal primers. Conventionally, the templates are amplified by PCR or bacterial culture, purified, and sequenced. The method of the present invention makes it possible to pick a virally infected bacterial plaque or cell, amplify the template with a labeled primer in the presence of dNT$^\alpha$Ps, and, after exonuclease digestion, load the samples onto a gel. The time savings is substantial because the purification and cycle sequencing steps are replaced with a simple exonuclease digestion.

(ii) Alu PCR takes advantage of the ubiquitous Alu repeat sequence in human DNA to design PCR primers that amplify human DNA (Nelson et al, *Proc. Natl. Acad. Sci. USA* 86:6686 (1989)). The technique has been useful for amplifying inter-Alu sequences from somatic cell hybrids and from flow-sorted chromosomes (Nelson et al, *Proc. Natl. Acad. Sci. USA* 88:6157 (1991); Cotter et al, *Genomics* 9:473 (1991)). The one-step procedure of the invention makes it possible to amplify Alu PCR products that can be sequenced or cloned directly. That is, the products can be sequenced by the usual exonuclease III digestion method, or, by simply omitting the digestion, the PCR products can be cloned.

(iii) One focus of the human genome project is a global survey of human genetic diversity (Cavalli-Sforza et al, *Genomics* 11:490 (1991); Baer, *Human Biology* 65:7 (1993)). Direct sequencing of PCR products makes it possible to perform high-resolution analysis of many individuals from a variety of geographic locations (Ritte et al, *Human Biology* 65:359 (1993)). For example, mitochondrial DNA, amplified from single plucked human hairs, has been used to determine the population diversity among individuals of an aboriginal African community (Vigilant et al, *Proc. Natl. Acad. Sci. USA* 86:9350 (1989)). The one-step procedure of the invention is ideally suited for such studies because: (1) few primers are required because only a few selected genomic markers are chosen to be amplified, and (2) template DNA is virtually unlimited because of the ease of collection and stability of human hair. Therefore, the rate of population diversity data collection can be increased by the time-savings method of the invention.

(iv) The procedure of the invention can also be applied to disease diagnosis. For example the majority of individuals afflicted with cystic fibrosis carry a characteristic three-base deletion, termed $\Delta F_{508}$ (Riordon et al, *Science* 245:1066 (1989); Bat-sheva et al, *Science* 245:1073 (1989)). Individuals can be tested for the $\Delta F_{508}$ deletion by analysis of heteroduplex DNA (Rommens et al, *Am. J. Hum. Genet.* 46L395 (1990)). However, some individuals have the cystic fibrosis phenotype but do not carry the $\Delta F_{508}$ deletion; thus the genotype of these individuals must be determined by sequencing (Shoshani et al, *Genomics* 15:236 (1993); Lucotte and Loirat, *Meth. Enzymol.* 155:166 (1993)). The present method can accelerate the rate of genotyping of individuals that are either diseased or are carriers, but that do not show the $\Delta F_{508}$ deletion. Many other diseases that can be diagnosed by sequencing would benefit from the time-savings of the present method. Likewise, the present invention can be applied in forensics, and evolutionary biology.

In contrast to methodologies of the art, the entire one-step PCR sequencing procedure of the invention is amenable to automation. The procedure requires only four processes (as described above) because the amplification and termination steps are accomplished simultaneously: (1) select templates, (2) amplify incorporating the sequence-delimiting modified dNTP's, (3) digest with exonuclease to unmask the modified dNMP's, and (4) separate and detect the DNA fragments. Processes 2 and 3 are "one pot" reactions; therefore, no human intervention is necessary beyond selecting the template and providing a robotic workstation with reagents. One skilled in the art will appreciate that the need for four separate amplification reactions can be avoided by selecting polymerases, produced, for example, by site directed mutagenesis, that are specific for one of the bases present in the nucleotide to be incorporated and including each such polymerases in the same reaction vessel.

The ABI CATALYST 800 Molecular Biology LabStation, for example, is well-suited to perform the present method automatically. It is designed specifically to perform sequencing reactions and is pre-programmed to perform cycle sequencing (some modification of the CATALYST software would be required).

Upon completion of the exonuclease step of the present procedure, the samples are, advantageously, loaded onto a gel (the Bio-Rad Gene Loader II, for example, can load gels automatically). If radioactive or chemiluminescent labels are used, one sample is, advantageously, loaded per lane. The advantage of a radioactive label is the simplicity of 5' end-labeling the primer by polynucleotide kinase. Alternatively, a chemiluminescently-labeled primer (or other non-radioactively labeled primer) makes it possible to avoid the contamination and disposal problems associated with radioactively-labeled samples. Additionally, the present one-step sequencing protocol can be expected to be compatible with multiplex sequencing in which labeling is accomplished, after transfer of the gel to a solid support, by hybridization to a radioactively—or chemiluminescently-labeled probe (Church and Gilbert, *Proc. Natl. Acad. Sci. USA* 81:1991 (1984); Church and Kieffer-Higgins, *Science* 240:185 (1989)).

Fluorescent labeling options are: (1) incorporation of fluorescently-labeled chain termination during polymerization (Dye-deoxy terminators, ABI) or (2) utilization of pre-labeled fluorescently-labeled primers. Since the present procedure requires that the 3' ends of the product molecules be removed by exonuclease, the fluorescent labels are, advantageously, attached to the primers prior to amplification. In the simplest case, one primer is labeled per base-specific reaction and the G, C, T, and A samples are loaded in separate lanes. However, the ABI373A sequencer, for example, is capable of sequencing all four bases in a single lane, and the present method is adaptable to one-lane sequencing.

Fluorescently-labeled boronated triphosphates can serve both as label and sequence deliminaters in the present processes. Synthesis of such triphosphates can be carried out as follows. The first step is the attachment of the 3-amino-1-propyn-1-yl linker arm to the 5 position following the procedure of Robins et al. The 5'-phosphate residues are then attached in three successive steps following Tomasz et al (Angew. Chem. Int. Ed. Engl. 31:1373 (1992)). The crucial step is the treatment with pyridine-borane to effect boronation of the phosphate; however, as a result of the low reactivity of pyridine-borane, reduction of the propynyl moiety of the linker is highly improbable. Slightly alkaline treatment of the Lewis-base borane formed in this reaction will result not only in the elimination of the β-cyanoethyl group from the phosphorous, but also in selective 3'-O-deacetylation. After building-up the 5'-boronated-triphosphate residue, the N-trifluoroacetyl protecting group will be removed from the linker. The diastereomers can be separated either before or after this step. Finally, the peptide bond is formed between the carboxyl group of the appropriate succinimidylfluorescein dye (Applied Biosystems) and the amino group of the linker, followed by removal of the acetyl protecting group from the phenolic hydroxyl function of the dye. (Alternative linkers can be designed (eg a n-carbon alkyl chain) using standard chemistries (see Zaratova et al, Nucleosides and Nucleotides 10:295 (1991) and Vincent et al, Nucleic Acids Res. 10:6787 (1982)).

In order to employ one-lane sequencing with the present method, the PCR primers are labeled with base-specific (eg, fluorescent) tags. For example four fluorescent phosphoramidite labels can be obtained from ABI that can be attached to the 5' end of oligonucleotides during solid phase synthesis; therefore, all four bases can be sequenced in a single lane. Further, because in the present method PCR amplification and incorporation of sequence delimiters are accomplished simultaneously, the method has the potential to sequence, bi-directionally, both strands of the PCR product in a single lane.

The rationale for bi-directional one-lane sequencing is as follows. Each position of a sequencing gel ladder can be thought of as an array of binary data in which either a band is present (1) or absent (0) (Nelson et al, Nucl. Acids. Res. 20:1345 (1992)). A four lane, one label sequencing gel (or likewise, a one lane, four label gel) represents each base by the presence of a band at each position, for example: A=(1,0,0,0), T=(0,1,0,0), G=(0,0,1,0), C=(0,0,0,1). However, a binary system with four lanes (or labels) is capable of determining $2^n-1$ outcomes (to avoid the null outcome). Therefore, the four bases of each strand can be represented by a unique combination of four labels, for example: $A_1$=(1,0,0,0), $T_1$=(0,1,0,0), $G_1$=(0,0,1,0), $C_1$=(0,0,0,1), and $A_2$=(1,1,0,0), $T_2$=(0,1,1,0), $G_2$=(0,0,1,1), $C_2$=(1,0,0,1). Consequently, the two primers can be labeled with a combination of the four different fluorescent labels and used separately in base-specific reactions that, after pooling, make it possible to sequence all four bases of both strands of the DNA template in a single lane.

In order for the reaction products of the invention to be loaded directly onto a gel, a relatively high concentration of labeled primer is advantageously present during amplification. The results shown in FIG. 2 were obtained from a 25 μl reaction that was concentrated by precipitation prior to loading. It is noted that ABI has developed a low-volume method for fluorescent sequencing (Prism). In their method, the total amount of primer is held constant but the concentration is increased from 0.4 pmol/μl to 1.2 pmol/μl, thus allowing sequencing reactions to be pooled, mixed with loading buffer, and loaded directly onto a gel. It is noted that 0.4 pmol/μl is the same concentration used the presently described protocol. Therefore, increasing the primer concentration of the present protocol by a factor of 3, while reducing the volume to 5–10 μl, should allow the reactions to be loaded directly onto a sequencing gel.

In any series of PCR amplification experiments, carryover of PCR products from prior experiments is a concern. The most effective prevention of contamination is to separate physically the PCR reactants from the products (Kwok, PCR Protocols: A guide to Methods and Applications, pp. 142–145, Academic Press (1990)). However, physical separation is not possible when using the CATALYST 800 robot because both the piper tip and the reaction wells are reusable. Since the present invention includes PCR amplification with sequencing, the procedure will be sensitive to contamination by PCR products. Therefore, after each experiment, the pipet tip and reaction wells could be removed from the CATALYST and washed thoroughly or decontaminated by some other method.

In addition to the one step procedures described above, boronated triphosphates can also be employed to extend the usefulness of strand displacement amplification (SDA) (Walker et al Proc. Natl. Acad. Sci. USA 89:329–396). SDA accomplishes in vitro DNA amplification by utilizing specific properties of 2'-deoxyadenosine 5'-α-thio-triphosphate, ie, it can be incorporated into DNA by exonuclease-free Klenow and, once incorporated, it is resistant to digestion by the restriction enzyme HincII. The resistance to digestion results in a primer extension product which is nicked at the synthetic primer site, but unaffected at the sites of 2'-deoxyadenosine 5'-α-thio-triphosphate incorporation; thus the protected strand becomes available to serve as the template for subsequent cycles of amplification. However, the applicability of SDA is limited because only relatively short DNA fragments (<100 bp) can be amplified and the procedure exhibits a sequence specificity which prevents amplification of certain regions of DNA. The limitations of SDA are probably due, in part, to the relatively poor incorporation efficiency of 2'-deoxyadenosine 5'-α-thio-triphosphate. Since the boronated compounds are resistant to nucleases and are very good substrates for exonuclease-free Klenow, ie the efficiencies of incorporation by exonuclease-free Klenow ($V_{max}/K_m$) are comparable to their natural counterparts, both the length of amplified fragments and the variety of target sequences can be expected to be increased by substituting boronated triphosphates directly into the SDA procedure.

Boranophosphates can also be used in long range PCR sequencing and closure. The conventional methods for long range sequencing and closure are primer walking and the cloning of sets of unidirectional nested deletions. Boranophosphates provide an alternative to these techniques. It has been shown recently that very long DNA duplexes can be produced by PCR (Barnes, Proc. Natl. Acad. Sci. USA 91:2216 (1994)); both an exo+ and an exo-thermostable polymerase were used in the PCR reaction. (Taq (exo−) and Deep Vent (exo+) have been used to amplify efficiently a 13-kb region from phage T7 DNA. Amplification was achieved in high yield with all normal dNTPs as well as with successive addition of the boronated dNTPs (2.5 μM).) Since a maximum of 1-kb of DNA can be sequenced by the best of sequencing runs, both strands of a duplex of a greater size could not be sequenced directly by conventional techniques. However, the use of boronated dNTPs in the amplification provides a means of sequencing without the need for an intermediate primer walking or nested deletion step.

In accordance with this embodiment of the present invention, a long amplified duplex is fragmented using a restriction enzyme(s) and the fragments separated, for example, by agarose gel electrophoresis. The restriction fragments can be, for example, cut out of the gel and labeled by back-filling at a 5' overhang. After labeling (eg, at the 3' end), the boronated sequence delimiters are revealed by a 5' exonuclease that acts on double stranded DNA, such as T7 gene 6- or μ- exonuclease. The boranophosphates are resistant to these 5' exonucleases, as shown in Example 9 (see also Thatcher et al, J. Org. Chem. 58:2272 (1993)). Thus, once the long DNA duplexes are amplified, restricted into smaller fragments, labeled by back-filling, and digested by exonuclease, the fragments can be, for example, loaded directly onto a polyacrylamide gel and sequenced. The number of manipulations involved in this procedure is about the same as needed for current methods for preparing sets of nested primers and cloning, however, in the present case, the sequence of the DNA is obtained. It will be appreciated that, in addition to using double-strand specific 5' exonucleases, the strands can be denatured and then single-strand specific exonucleases (eg phosphodiesterase II) used. It is also noted that boranophosphates provide a ready way to produce a set of nested deletions for cloning. Random incorporation of boranophosphates during PCR followed by exonuclease III provides nested sets of deletions that terminate at a boranophosphate. These fragments can be ligated into cloning vectors. The lengths of the fragments can be determined statistically by the percentage of boron doping.

Boronated-triphosphates (ribo or deoxyribo) can also be used in the preparation of aptamers. Aptamers are oligonucleotide ligands selected from a combinatorial "shape" library to fit a target (which can be a small molecule like caffeine or theobromine, or a large molecule like a protein, oligosaccharide, oligonucleotide, enzyme, antibody, receptor or other regulatory molecule (see Kenan et al, TIBS 19:57 (1994); Szostak TIBS 17:89 (1992); Green et al, Science 258:1910 (1992); Wang et al, Biochemistry 32:1899 (1993); Tuerk et al, Science 249:505 (1990); Beaudry et al, Science 257:635 (1992)). DNA and RNA are capable of mimicking the shapes of proteins and other molecules, and their ability to be amplified by PCR makes it possible to select one molecule from a population of $10^{15}$ molecules prepared by production of random combinations of building blocks at every position of a macromolecule. However, a limitation of nucleic acids is that there are only 4 naturally occurring monomer units from which to assemble complex oligomeric ligands. Since boronated triphosphates are good substrates for PCR, they are suitable for aptamer assembly, thereby providing 4 additional building blocks. Therefore, boronated triphosphates (of both RNA and DNA, as well as with modified bases) increase the variety of ligands that can be produced by aptamer technology.

In accordance with this embodiment of the present invention, boronated triphosphates (ribo or deoxyribo) are used as monomer units for production of a nucleic acid (DNA or RNA) shape library by PCR. The library is designed to have degeneracy at a number of different positions in the oligonucleotide. The combinatorial library is screened for selection against a target surface. Selected ligands that bind to the target are partitioned from those unbound, producing a population of molecules that is enriched in binding affinity to the target. The enriched population is amplified by PCR. By subjecting the enriched population to further rounds of binding, higher affinity ligands are progressively selected. These progressive cycles of amplification and reselection produce optimized ligands, or aptamers.

In addition to amplification/sequencing protocols, nucleic acids containing modified nucleotides of the type described herein, advantageously boronated nucleic acids, can be used to probe the interaction of nucleic acids with other cellular components. One skilled in the art will appreciate that nucleic acids containing modified nucleotides (eg boronated nucleotides) can be used in electron spectroscopic imaging (Bendayan et al, J. of Histochem Cytochem 37:573 (1989)) and electron energy loss spectroscopy (Colliex, Ann. NY Acad. Sci. 483:311 (1986); Ottensmeyer, J. Ultrastruct. Res. 88:121 (1984) and 72:336 (1980)).

Further to the above, α-borano triphosphates can be expected to be useful for direct gene transfer regimens. The properties of α-boronated triphosphates that can be utilized to sequence DNA, ie the compounds can be incorporated into DNA by polymerases and, once incorporated, are resistant to nucleases, can also be used in direct gene transfer. In direct gene transfer, DNA that includes a promoter, a gene of interest, and a terminator is injected, for example, into muscle tissue (Wolff et al, Science 247:1465–1468 (1990)). The introduced genes can be transcribed into RNA and translated into proteins that can perform a variety of pharmacological functions. For example, such proteins have been shown to: modulate the hormonal levels of cardiac tissue in rats (Kitsis et al, Proc. Natl. Acad. Sci. 88:4138–4142 (1991)), express foreign genes in fish (Hansen et al, FEBS Letters 290:73–76 (1991)), express human dystrophin in mice (Acsadi et al, Nature 352:815–818 (1991)), elicit an immune response to a foreign protein in mice (Tang et al, Nature 356:152–154 (1992)), and elicit protection against the influenza virus in mice (Ulmer et al, Science 259:1745–1748 (1993)). Expression of the injected genes can be detected over long periods of time, ie several months, even though the DNA is degraded rapidly in blood serum. Since α-borano trisphophates can be incorporated into DNA by polymerases, the stability that they exhibit towards nucleases should increase the lifetime of the injected DNA and thereby increase the efficacy of the direct gene transfer method.

Certain aspects of the present invention are described in greater detail in the non-limiting Examples that follow.

EXAMPLE 1

Synthesis and Purification of 2'-Deoxynucleoside 5'-α-Borano-Triphosphates

A representative α-P-borane-substituted 2' deoxynucleoside 5'-triphosphate, eg, α-P-borano-thymidine 5'-triphosphate has been synthesized by Tomasz et al (Angew. Chem. Int. Ed. Engl. 31:1373 (1992)). The crucial step in the synthesis of the borano-triphosphates is the attachment of the $BH_3$ group to the P atom. This reaction was performed at the stage of nucleoside 5'-phosphoramidite by using an exchange reaction with an amine-borane. The $N_1O^{3'}$-acylated 2'-deoxynucleoside was phosphitylated by (2-cyanoethyl)(N,N-diisopropyl)phosphoramidic chloride to the respective 5'-phosphoramidite derivative. The 5'-phosphoramidite was treated in situ with excess pyridine-borane in DMF at 45°–50° C. for 24 h. (Of the amine-boranes studied, pyridine-borane was the only one that selectively entered into reaction with the phosphorus and did not reduce the base residues.) After ammoniacal treatment, 2'-deoxynucleoside 5'-borano-N,N-diisopropylphosphoramidate was isolated by ion-exchange column chromatography. Reaction of these phosphoramidate derivatives with excess bis-tri-n-butylammonium pyrophosphate gave (after ion-exchange chromatographic purification) the mixture of α-P-borane-substituted 2'-deoxynucleoside 5'-triphosphate diastereoisomers in overall yields of 5-6%. The diastereoisomers were separated by HPLC (both diastereoisomers can be incorporated using thermostable polymerases, the stereoisomer that is first eluting on HPLC (Tomasz et al, Angew. Chem. Int. Ed. Engl. 31:1373 (1992)), however, appears to be the better substrate for DNA polymerase; both diastereoisomers are resistant to both 5' and 3' exonuclease, but to different extents depending on the enzyme).

The method of synthesis has been applied to the preparation of α-P borano derivatives of the other three (i.e., A, G, and C) 2'-deoxynucleoside 5'-triphosphates by modification of the procedure.

EXAMPLE 2

Optimization of Incorporation of dNT$^b$Ps and Exonuclease Digestion

Optimization of reaction conditions (incorporation and digestion) results in a uniform and complete set of bands for each base-specific sequencing lane. Ideally, a single dNT$^b$P is incorporated into each product molecule such that each position of the PCR product is represented equally. Exonuclease III digestion can be optimized so that each molecule is digested only to, and not beyond, the dNM$^b$P.

A. Incorporation

The incorporation efficiency ($V_{max}/K_m$) of each of the dNT$^b$Ps can be determined by kinetic analysis (Randall et al, J. Biol. Chem. 262:6864 (1987); Boosalis et al, J. Biol. Chem. 262:14689 (1987)). The kinetic parameters have been determined for a different type of boronated dNTP, the base-boronated N$^7$-cyanoborane-2'-deoxyguanosine 5'-triphosphate. For incorporation by exonuclease-free Klenow, it has been found that the base-boronated 2'-deoxyguanosine 5'-triphosphate has a similar $V_{max}$ but a lower $K_m$ than the normal dGTP. For the present invention, a larger or smaller $K_m$ for the dNT$^b$Ps with respect to the normal dNTPs can be compensated for by a change in the ratio of the concentrations of normal to boronated triphosphates in the PCR reaction. As is shown in Example 3, the boronated triphosphates appear to be governed by such a $K_m$-dominant incorporation, because the appropriate changes in the ratio of [dNTP] to [dNT$^b$P] during PCR amplification results in uniform and faithful incorporation.

The kinetic parameters for incorporation by Vent or other heat stable DNA polymerases can be determined and the incorporation parameters for all four dNT$^b$Ps thereby rationally optimized. Alternatively, the ratios of boronated to normal triphosphates and their concentrations can be varied in a trail and error fashion.

Kinetic analysis

The $K_m$ and $V_{max}$ for incorporation of dNTPs and dNT$^b$Ps can be determined by a labeled primer-template/polyacrylamide gel assay (Randall et al, J. Biol. Chem. 262:6864 (1987); Boosalis et al, J. Biol. Chem. 262:14689 (1987)). The system consists of a radioactively-labeled synthetic primer annealed to a synthetic template that is designed to code for the selected dNTP or dNT$^b$P at the first position of primer extension. Primer extension is performed for a range of substrate concentrations. The extension products are separated by denaturing PAGE and quantitated on a Molecular Dynamics phosphorimager. At steady state conditions, the initial reaction velocities ($v_i$) can be determined from the integrated band intensities. The intensity of the extended product ($I_1$) divided by the intensity of the unextended primer ($I_o$) plus one half the intensity of the extended product (0.5 $I_1$) gives a measure of $v_i$ (Petruska et al, Proc. Natl. Acad. Sci. USA 85:6252 (1988)).

An example of the protocol that can be followed to determine the kinetic parameters for the base-boronated N$^7$-cyanoborane 2'-deoxyguanosine 5'-triphosphate ($^{7b}$dGTP) is as follows. For the normal and boronated dGTP, a primer (5'-CAGGAACAGCTATGGCCTCA-3' (SEQ ID No: 3); 30 pmol) is end-labeled with 10 μCi of γ$^{33}$ P-ATP, annealed to an equal amount of a template (5'-GTGTAGCTGAGGCCATAGCTGTTCCTG-3'(SEQ ID NO: 4); 30 pmol), and mixed with Vent or Taq DNA polymerase (conditions for use with Taq polymerase are as described below except as otherwise noted in brackets) in buffer A (10 mM Tris-HCl, pH 8.9, 50 mM NaCl, and 0.1% TRITON X-100(a non-ionic detergent); 32.5 μl). The primer is extended by mixing 5 μl of the primer/template duplexes with 5 μl of various concentrations of dGTP or $^{7b}$dGTP in buffer B (10 mM Tris-HCl, pH 8.9, 50 mM NaCl 0.1% TRITON X-100, and 10 mM MgSO$_4$) [10 mM Tris-HCl, pH 8.9; 50 mM NaCl and 5 mM MgCl$_2$]. The reaction is carried out for 1.5 min at 76° C. [72° C.] and stopped by addition of 10 μl of loading buffer (95% formamide, 20 mM Na$_2$EDTA, 0.1% bromophenol blue, 0.1% xylene cyanol). The samples are separated on a 16% polyacrylamide/7 M [8 M] urea sequencing gel and the intensities of the bands are quantitated on a Molecular Dynamics phosphorimager. The $K_m$ and $V_{max}$ can be calculated from the initial reaction velocities by nonlinear regression analysis. To verify that the initial velocities are obtained at an enzyme-limiting condition, the amount of enzyme is adjusted to produce about 20% extension at the highest substrate concentrations.

Time course reactions

That the initial velocities are obtained during the period of linear accumulation of product can be verified by performing a time course experiment for the highest concentrations of substrate. Labeled primer/template and Vent DNA polymerase in buffer A (32.5 μl) are mixed with dGTP or $^{7b}$dGTP in buffer B (32.5 μl) at 76° C. Aliquots are withdrawn at 30 sec intervals and mixed with loading buffer. The intensities of the bands can be quantitated and a percent extension vs. time plot can be generated.

Additional considerations

Vent polymerase includes a 3'exonuclease activity that results in a higher incorporation fidelity relative to exonuclease-free heat-stable polymerases (Eckert and Kunkel, PCR Methods and Application 1:17 (1991)). However, due to the additional exonuclease activity, the kinetic analysis measures apparent $K_m$ and $V_{max}$ values that are functions of both the polymerization and the exonuclease activities. The apparent kinetic parameters should aid in optimization of the procedure of the present invention because the relative kinetic parameters need only be compared among the boronated and normal dNTPs (Rappaport, Biochemistry 32:3047 (1993); Singer et al, Biochemistry 28:1478 (1989)). It is also noted that the polymerization temperature may cause denaturation of the synthetic primer/template duplex. If it proves to be a problem, the length of the oligomers can be increased.

B. Exonuclease digestion

Exonuclease digestion can be optimized so that each PCR product is digested only to, and not beyond, the first dNM$^b$P.

To render the present method a truly one-step procedure, the digestion should take place immediately following amplification and directly in the PCR reaction mixture.

In preliminary experiments, the buffer, time, and temperature of the exonuclease reaction have been adjusted. Exonuclease III from Bethesda Research Laboratories was found to be superior to that from other vendors (Guo and Wu, *Nucl. Acids Res.* 10:2065 (1982); Henekoff, *Gene* 28:351 (1984)). Enzyme concentration, time, and temperature of digestion were determined empirically. The buffer composition was determined by modifying the manufacturer-supplied buffer (50 mM Tris-HCl, pH 8.0, 5 mM $MgCl_2$, and 1 mM DTT). Tris-HCl, concentration and pH were varied systemically and 50 mM and pH 7.5 were found to be optimal. Twenty-five units of exonuclease III in a buffer containing 50 mM Tris-HCl, pH 7.5, 5 mM DTT, and 5 mM $MgCl_2$ digested satisfactorily the PCR products in 45 min at 37° C. One hundred units of enzyme effected satisfactory digestion in 30 min under the same conditions, however, in the case of $dCM^bP$-containing samples, 25 units of enzyme is sufficient. Under these conditions, almost all of the normal dNMPs were digested while the boronated dNMPs were not.

While the preliminary experiments described herein were performed on PCR products that had been ethanol-precipitated prior to exonuclease treatment, conditions can be established that allow direct digestion of the PCR products.

EXAMPLE 3

Amplification and Sequencing of Region of M13mp2 Phage DNA

Materials

The 2'-deoxynucleotides dA, dT, dC, and dG 5'-α-borano-thiotriphosphates were synthesized by the methods described in Tomasz et al, *Angew. Chem. Int. Ed. Engl.* 31:1373–1375 (1992)). Oligonucleotides were synthesized on an ABI 380B DNA synthesizer, purified by denaturing PAGE, and recovered by electroelution. The thermostable DNA polymerase, Vent, was purchased from New England Biolabs. M13mp2 DNA was provided by Ted Gonzalez, Duke University. (Frederico et al, *Biochemistry* 29:2532 (1990)). $\gamma^{33}$P-ATP (>1000 Ci/mmol) was purchased from Amersham.

Labeling of Primer 1

Primer SS20 (5'-TATCGGCCTCAGGAAGATCG-3' (SEQ ID NO: 15) complementary to positions 6467 to 6448 of M13mp2; 20 pmol) was 5' end-labeled with $\gamma^{33}$P-ATP (20 μCi) and polynucleotide kinase (New England Biolabs; 10 units) in the manufacturer-supplied buffer (10 μl).

Polymerase Chain Reaction (+)M13mp2 DNA template (0.5 pmol) was mixed with labeled primer SS20 and unlabeled primer 2 (5'-TCACACAGGAAACACTATGC-3(SEQ ID NO: 6); positions 6200–6221 of M13mp2; 20 pmol each), dATP, dTTP, dCTP, and dGTP (100 μM of each), and one of each $dAT^bP$ (5 μM), $dTT^b1P$ (5 μM), $dCT^bP$ (100 μM), or $dGT^bP$ (2.5 μM) in PCR buffer (50 mM NaCl, 2 mM $MgSO_4$, 0.1% TRITON X-100, and 10 mM Tris-HCl, pH 8.9, at room temperature). The reaction mixture was heated to 95° C. for 1 min and returned to ice. Vent DNA polymerase (0.5 μl; unit) was added and the PCR was performed in an Ericomp thermal cycler for 25 cycles of 95° C. for 1 min, 56° C. for 1 min, and 76° C. for 1 min.

Exonuclease III digestion

Following PCR amplification, the DNA was ethanol-precipitated, then resuspended in 10 μl of deionized water.

An aliquot (5 μl) was digested with exonuclease III (25 units) in buffer (50 mM Tris-HCl, pH 7.5, 5 mM DTT, 5 mM $MgCl_2$; 10 μl total) for 45 min at 37° C.

Electrophoresis

Denaturing loading buffer (95% formamide, 0.1% bromophenol blue, 0.1% xylene cyanol, and 20 mM $Na_2EDTA$; 10 μl) was added to each sample which was then loaded onto a 12% polyacrylamide/8 M urea gel and run for 2 hours at 75 W in TBE buffer (89 mM Tris-borate, 2 mM $Na_2EDTA$, pH 8.0). The gel was dried under vacuum and the signal was detected by autoradiography.

As shown in FIG. 2 (see also FIG. 3), the results obtained, using conditions that had not been optimized, revealed that the boronated $dCT^bP$ produced a uniform and faithful ladder for 70 bases past the primer, while dG, dA, and dT 5'-α-borano-triphosphates produced a strikingly uniform and faithful sequencing ladder beginning at the 3' end of the labeled SS20 primer and extending about 195 bases into the M13 genome.

The sequencing ladders for dG, dA, and dT 5'-α-borano-triphosphates were clear, uniform, and easy to read. The only ambiguities were:

$dGT^bP$—a missing band at position 187 and an extra band at position 93.

$dTT^bP$—missing bands at positions 92, 126, and 142 and extra bands at positions 34 and 35.

$dAT^bP$—a missing band at position 65 and extra bands at positions 73 and 87–89.

For the 195 bases (215 bases past the 20 base primer) that were sequenced by dG, dT, and dA, each position was scored for each 2'-deoxynucleotide (that is, the presence or absence of a band at the correct positions). Therefore, the accuracy for each base in this preliminary experiment was:

$dGT^bP$—99.0% correct.

$dTT^bP$—97.5% correct.

$dAT^bP$—97.5% correct.

$dCT^bP$—100% correct for 70 bases.

Missing bands in the sequencing ladders were probably due to sub-optimal incorporation conditions. By determining the kinetic parameters for incorporation of each $dNT^bP$, using protocols such as those described in Example 2, optimal conditions for incorporation can be employed in the one-step procedure that should eliminate sequencing errors due to missing bands and allow for longer reads. Alternatively, use of another boronated modified base could be employed.

Extra bands in the sequencing ladders were probably due to incomplete exonuclease III digestion. The correct conditions for digestion can be determined by simple time course of digestion experiments, if necessary, the kinetic parameters for exonuclease III digestion can be determined by the labeled primer-template/polyacrylamide gel assay (Otto et al, *Biophys. J. Abstracts*, 37th Annual Meeting, Tu-Pos278, pp. A181). Alternatively, another 3' to 5' exonuclease can be employed.

The incorporation and/or exonuclease III digestion properties of $dCT^bP$ seem to be different from other three $dNT^bPs$. It is possible that the relative incorporation efficiency of $dCT^bP$ is low, resulting in too few incorporated sequence delimiters. Alternatively, it is possible that, once incorporated, the $dCM^bP$ residues are not as resistant to exonuclease III digestion, thereby allowing digestion of the longer fragments. It is also possible that the $dCT^bP$ preparation was not pure or that the compound could have degraded before use. However, after optimization of both incorporation and exonuclease III digestion, $dCT^bP$ can be expected to produce longer reads of sequencing data.

EXAMPLE 4

(A) Incorporation of Boronated Nucleotides in PCR Products and (B) Base Specific Resistance of Extended Primers to Exonuclease Activity A. Incorporation of Boronated Nucleotides Materials. The 5'-α-borano-triphosphates of dA, dT, dC, and dG were synthesized and the diastereomers were HPLC-separated by modifications of the methods described in Tomasz et al (Angew. Chem. Int. Ed. Engl. 31:1373 (1992)). Normal oligonucleotides to be used as primers were purchased from Genset, purified by TLC (USB), and recovered by lyophilization. The thermostable DNA polymerases, Vent and Taq, were purchased from New England Biolabs and Boehringer Mannheim. γ-$^{33}$P-ATP and α-$^{33}$P-dATP (>1000 Ci/mmol) were purchased from Amersham.

Polymerase Chain Reaction. Phage T7 DNA template (5 ng) was mixed with 20 pmol primers (T7$_{for}$: 5'-GGAGCGTAGGAAATAATAC-3' (SEQ ID NO: 7) and T7$_{rev}$: 5'-CGGTTTTAATTACGTTAGCC-3' (SEQ ID NO: 8)), dATP, dTTP, dCTP, and dGTP (100 μM of each), and one of each dAT$^b$P, dTT$^b$P, dCT$^b$P, or dGT$^b$P (2.5 μM each) in Vent PCR buffer (50 mM NaCl 2 mM MgSO$_4$, 0.1% TRITON X-100, and 10 mM Tris-HCl, pH 8.9 at room temperature). The reaction mixture was heated to 95° C. for 1 min and returned to ice. Vent DNA polymerase (1 μL; 2 units) was added and the PCR was performed in an Ericomp thermal cycler for 25 cycles of 95° C. for 1 min, 53° C. for 1 min, and 76° C. for 1 min. An aliquot of each extended primer-template duplex (10 μL) was digested with exonuclease III (0.5 μL, 32.5 units) for 30 min at 37° C.

Electrophoresis. Samples were separated on a 1% agarose gel.

Figure 4:
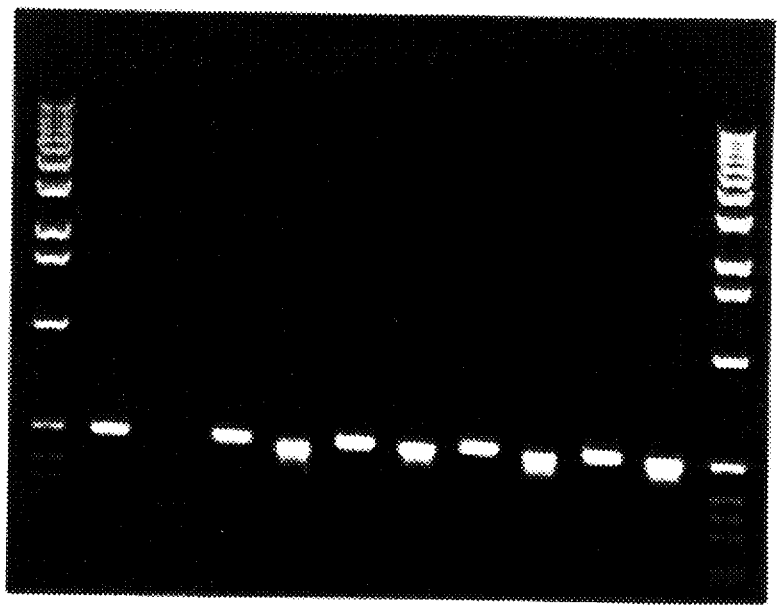
FIG. 4. dNT$^b$P's as substrates for PCR.

From FIG. 4, it can be seen that both normal and boronated nucleotides produced comparable amounts of DNA (compare lane 1—all normal, with lanes 3, 5, 7 and 9-partially boronated). A full length product (509 bp) is present in all lanes, indicating that boron does not inhibit PCR amplification.

To demonstrate that the PCR product indeed contained boronated nucleotides and to determine if these nucleotides conferred resistance to nuclease, the PCR product was digested with exonuclease III as seen in FIG. 4. Upon digestion, the normal DNA was digested extensively (lane 2), whereas the boron-containing DNA was digested very little, demonstrating that boron was incorporated into the DNA (lanes 4, 6, 8 and 10).

B. Base Specific Resistance of Extended Primers to Exonuclease Activity

Labeling. Primer (5'-CAGGAACAGCTATGGCCTC-3' (SEQ ID NO: 9); 10 pmol) was 5' end-labeled with γ-$^{33}$P-ATP (20 μCi) and polynucleotide kinase (10 units) in the manufacturer-supplied buffer (10 μL).

Extension and digestion. Labeled primer was annealed to an equal amount of unlabeled template (5'-GTGTAGCTGAGGCCATAGCTGTTCCTG-3' (SEQ ID NO: 10); 10 pmol). Extension was accomplished with T4 DNA polymerase (1 unit) in the presence of (a) all normal dNTPs or (b) successive replacement of one dNTP with the corresponding dNT$^b$P (50 μM each in buffer: 50 mM Tris-HCl, pH 7.5, 10 mM MgCl$_2$ 1 mM DTT; 25 μL) for 10 min at 37° C. An aliquot of each extended primer-template duplex (10 μL) was then digested with exonuclease III (0.5 μL; 32.5 units) for 30 min at 37° C.

Electrophoresis. Denaturing loading buffer (95% formamide, 0.1% bormophenol blue, 0.1% xylene cyanol, and 20 mM Na$_2$EDTA; 10 μL) was added to each sample which was then loaded onto a 16% polyacrylamide/8 M urea gel and run for 2 hours at 100 W in TBE buffer (89 mM Tris-borate, 2 mM Na$_2$EDTA, pH 8.0). The gel was dried under vacuum and the signal was detected by autoradiography.

As seen in FIG. 5, the primer was extended in the presence of all-normal nucleotides and, equally as well, by successive replacement of each nucleotide by 100% of the corresponding boronated nucleotide. In each case, the primer was extended the full length of the template (lane 2—all-normal, lanes 4, 6, 8 and 10—boronated). The presence of a significant quantity of boronated nucleotide (equal here to 4–11% of the total nucleotide concentration in the extended primer) did not affect the electrophoretic mobility of the extended primers.

Following extension, an aliquot of each sample was digested with exonuclease III. The all-normal product was digested to the limit of a duplex substrate (exonuclease III requires double stranded substrate, lane 3), whereas for each case in which a dNT$^b$P was substituted for a normal dNTP, exonuclease digestion was halted at the position of the boronated substitution (lanes 5, 7, 9 and 11). The boronated dA, dT, and dG (lanes 5, 7 and 9, respectively) were completely resistant to exonuclease III under these conditions, while the boronated dC was more susceptible to digestion (lane 11). This sensitivity parallels that seen for normal dC (Linxweiller et al, Nucl. Acids Res. 10:4845 (1982)). The differential sensitivity of dC has been compensated for by adding more dCT$^b$P (50 μM) to the sequencing reactions and by reducing the amount of exonuclease III from 100 units to 25 units. Thus, the above experiments demonstrate that (1) the boronated nucleotides allow for primer extension (where 3 out of 8 nucleotides, or 37%, of the newly synthesized product was boronated), (2) the boronated nucleotides are much more resistant to exonuclease III than normal nucleotides, and (3) the base-specific resistance implies that the bases are incorporated correctly.

EXAMPLE 5

One-Step Sequencing with End-Labeled Primer

Labeling of Primer 1. Primer T7$_{for}$ (5'-GGAGCGTAGGAAATAATAC-3' (SEQ ID NO: 7), positions 34534 to 34552 of phage T7) or primer T7$_{rev}$ (5'-CGGTTTTAATTACGTTAGCC-3' (SEQ ID NO: 8); complementary to positions 35042 to 35025 of phage T7; 20 pmol each) was 5' end-labeled with γ-$^{33}$P-ATP (20 μCi) and polynucleotide kinase.

Polymerase Chain Reaction. Phage T7 DNA template (5 ng) was mixed with 20 pmol of labeled and unlabeled primers, dATP, dTTP, dCTP, and dGTP (100 μM each), and one of each dAT$^b$P (2.5 μM), dTT$^b$P (10 μM), dCT$^b$P (10 μM) or dGT$^b$P (2.5 μM) in PCR buffer (50 μL). The reaction mixture was heated to 95° C. for 1 min and returned to ice. Vent DNA polymerase (1 μL; 2 units) was added and the PCR was performed in an Ericomp thermal cycler for 25 cycles of 95° C. for 1 min, 53° C. for 1 min, and 76° C. for 1 min.

Exo III digestion. Following PCR amplification, the DNA was extracted with chloroform:isoamyl alcohol (24:1), precipitated, and resuspended in deionized water (10 μL). An aliquot (5 μL) was digested with exo III (25 units) in buffer (50 mM Tris-HCl, pH 7.5, 5 mM DTT, 5 mM MgCl$_2$; 10 μL total) for 15 min at 37° C.

Electrophoresis. Denaturing loading buffer was added to each sample which was then loaded onto an 8% polyacrylamide/8 M urea gel and run for 2 hours at 100 W in TBE buffer. The gel was dried under vacuum and the signal was detected by autoradiography.

Results in FIG. 6 show that the sequence of about 350 base pairs (second loading not shown) of a 509 bp PCR product could be read. The α-P-borano dNTPs are thus incorporated faithfully into the correct positions of the DNA and, once incorporated, code for the correct complementary 2'-deoxynucleotide. If this were not true, then the background would have been blurry and the correct sequence could not have been obtained. The α-P-borano 2'-deoxynucleotides thus render the PCR products resistant, base-specifically, to exonuclease III, as evidenced by the correct sequencing ladder. By incorporating 2'-deoxynucleoside 5'α-P-borano-triophosphates into base-specific PCR reactions and then digesting the PCR products with exonuclease III, a uniform series of bands was produced, thereby defining the sequence of approximately 350 bases of a 509 base-pair PCR product.

The sequence data were remarkably clear and the bands were of quite uniform intensity. However, as is shown in FIG. 6A, there were two troublesome regions; one near position 34600 of the forward sequence and one near position 34915 of the reverse sequence, with bands across all four lanes. Because there were no pauses in the polymerization reaction (data not shown), it was hypothesized that these extra bands were most likely due to incomplete digestion. When the experiment was repeated, using samples that were digested with 130 instead of 25 units of exonuclease III (FIG. 6B), the extra bands near position 34600 of the forward strand disappeared completely, producing an easily readable sequence. The region surrounding position 34915 of the reverse strand was also clearer than had been observed previously; however, the correct sequence could not be read without ambiguity. Likely, there is a secondary structure associated with this region because (1) reagents, such as reagents, such as DMSO, which disrupt secondary structure also help to alleviate the sequence ambiguities, (2) with normal nucleotides, the exonuclease III pauses at this site, and (3) the pause is specific to this region and not to other sequences examined to date. The nuclease resistance is strand-specific, however, and thus the sequence of the other strand can be read. One alternative approach is to raise the temperature of the digestion, and thus melt out the secondary structure. If the exonuclease digestion were to be performed at high temperature, the secondary structure would be expected to be disrupted and digestion would produce uniform fragments at all sites.

EXAMPLE 6

Bi-directional One-Step PCR Sequencing with a Biotinylated Primer

Polymerase Chain Reaction. Phage T7 DNA template (10 ng) was mixed with 20 pmol of biotinylated (phi9$_{for}$ 5'-ACAGCTTCACCTGAGGCTATGG-3' (SEQ ID NO: 10); positions 21786–21807) and unmodified (phi9$_{rev}$ 5'-TCTTCGTTCTCCTCGTACTCACGC-3' (SEQ ID NO: 11); complementary to positions 22391–22414; 629 bp product) primers, dATP, dTTP, dCTP, and dGTP (100 μM of each), one of each dAT$^b$P (2.5 μM), dTT$^b$P (10 μM), dCT$^b$P (10 μM), or dGT$^b$P (2.5 μM), and 13 μCi α-$^{33}$P-dATP in Taq PCR buffer (10 mM Tris-HCl, pH 8.3, 50 mM KCl, 1.5 mM MgCl$_2$; 50 μL). The reaction mixture was heated to 95° C. for 1 min and returned to ice. Taq (5 units) and Deep Vent (0.005 units) DNA polymerases were added and the PCR was performed in an Ericomp thermal cycler for 25 cycles of 95° C. for 15 sc, 60° C. for 1 min, and 76° C. for 1 min.

Binding to magnetic beads. An aliquot of the PCR reaction (20 μL) was mixed with streptavidin-linked magnetic beads (Dynal; 10 mg/mL in 5 mM Tris-HCl, pH 7.5, 0.5 mM EDTA, 1 M NaCl; 20 μL) and incubated with mild agitation for 45 min.

Exonuclease III digestion. The PCR products bound to the magnetic beads were immobilized by a magnet and washed twice with exonuclease III buffer. The samples were resuspended in exonuclease buffer (10 μL) and digested with exonuclease III (60 units) for 30 min at 37° C.

Isolate unmodified primer strand fragments. After digestion, the samples were heated for 1 min at 95° C. to denature the PCR products. The magnetic beads, along with the biotinylated primer strand fragments, were immobilized with a magnet and the unmodified primer strand fragments were removed in the exonuclease buffer. The fragments were mixed with an equal volume of loading buffer and loaded buffer and loaded (6 μL) onto a sequencing gel (8% polyacrylamide/8 M urea).

Isolate biotinylated primer strand fragments. The biotinylated primer strand fragments were resuspended in loading buffer (10 μL) and heated for 1 min at 95° C. to detach them from the streptavidin-linked magnetic beads and then loaded (3 μL) onto a sequencing gel.

Electrophoresis. Performed as described for FIG. 6.

Cycle sequencing. As a control, cycle sequencing was performed on T7 DNA as directed in the Perkin Elmer Amplitaq cycle sequencing kit. The primers and T7 template DNA was the same as described below for the one-step method except that 1000 ng of highly purified template DNA was used for each cycle sequencing sample whereas only 10 ng were required for the present method.

A region of T7 DNA extending from the phi 9 promoter (629 bp product) was sequenced bi-directionally using the biotinylated primer—magnetic beads strategy (see FIG. 7). For comparison, the same region was sequenced using labeled primers by conventional cycle sequencing (see FIG. 7). For each method, the sequence could be read from approximately $A_{21900}$ to $G_{22350}$, or about 200–300 bases per strand from a single loading. No secondary structure-induced artifacts were noted for either the one-step or cycle sequencing method; however, each method had at least one position where the correct base could not be called because of an extremely weak band. In each case where a particular base could not be determined by one method, the base could be called correctly by the other method. The desirability of determining a sequence by two independent methods has been noted previously (Koop et al, Biotechniques 14:442 (1992)).

EXAMPLE 7

Suitability of Boronated Deoxynucleotide for Direct Gene Transfer

FIG. 8 shows that α-borano triphosphates can be incorporated by PCR into a duplex which contains a promoter (T7 phi 17) and a short downstream flanking region. When the boronated templates were use in an in vitro transcription system, the boronated templates were shown to produce RNA when the templates contained up to 75% boronated nucleotides. From FIG. 8 Upper panel, the correct 110 base PCR product was produced using, along with the other normal dNTPs, boronated dGTP (lane 3), boronated dCTP (lane 4), boronated dA (lane 5), boronated dG+dC (lane 6), boronated dC+dA (lane 8), and boronated dG+dC+dA (lane 9). Each of the PCR templates was capable of being transcribed into RNA and the amount of RNA was roughly proportional to the amount of DNA produced by PCR (corresponding lanes of the lower panel). Thus it appears that boronated deoxynucleotides do not inhibit transcription and therefore are suitable for use in direct gene transfer.

EXAMPLE 8

Resistance of Boronated DNA to Serum and Exonuclease Digestion, Transcription of Boronated DNA into mRNA and Translation of mRNA into Protein A. Resistance to degradation Equal amounts of normal and boronated (prepared using 100% boronated dCTP) PCR products (full length luciferase gene PCR amplified from plasmid (PROMEGA L482B); lucfor 5'TTGATGGAGCTGATACCGCTCG3' (SEQ ID NO: 12); lucrev 5'ATCTTCCCCATCGGTGATGTCG3' (SEQ ID NO: 13); Taq buffer: 10mM Tris (8.3), 50 mM KCl, 2.5 mM MgCl2; dNTPs: 100 micomolar each, Taq 5 units; plasmid DNA 5 ng; 25 cycles: 95 degrees C. (15 min.), 60 degrees C. (45 min), 72 degrees C. (1 min) and repeat) were incubated with 1/10 volume of mouse serum in buffer (50 mM NaCl, 5 mM MgCl$_2$, 5 mM DTT and 10 mM Tris, pH 7.6) at 37° C. for 20 min or for 40 min. As shown in FIG. 9A, full-length normal DNA was digested completely by 20 minutes (compare lane 2 (20 min) and lane 3 (40 min) with lane 1 (untreated)). Full length boronated DNA, however, persisted throughout the 40 min incubation (compare lane 5 (20 min) and lane 6 (40 min) with lane 4 (untreated)).

Approximately equal amounts of normal and boronated (prepared using 100% boronated dG or dC) PCR products (as above) were labeled and separated on a denaturing polyacrylamide gel (see FIG. 9B (lane 1 normal, lane 2 100% boronated dG, lane 3 100% boronated dC). Aliquots of each PCR product were digested with exonuclease III. As shown in FIG. 9B, normal DNA was digested by exonuclease III (compare lane 4 with lane 1), while boronated DNA was resistant to digestion (compare lanes 5 (dG$^b$) and 6 (dC$^b$) with lanes 2 and 3, respectively).

B. Transcription of boronated DNA into mRNA

Aliquots of PCR product (as above) were transcribed into mRNA using α$^{35}$S-ATP and the Promega TNT transcription/translation system. As shown in FIG. 9B, normal (lane 7) and boronated (lane 8—(100%)dG$^b$; lane 9 (100%) dC$^b$) were transcribed into full-length mRNA.

C. Translation of mRNA transcript into protein

Aliquots of normal and boronated PCR products (as above) were translated into protein using $^{35}$S-methionine and the Promega TNT transcription/translation system. The labeled protein was separated on an SDS-polyarylamide gel. As shown in FIG. 9C, full length protein was produced by both the normal (lane 1) and boronated (lane 2—boronated (100%) dG; lane 3—boronated (100%) dC) template.

In a separate study, normal and boronated templates were shown to be translated into functional enzyme at the same rate. PCR products containing all-normal, 100% boronated dG, or 100% boronated dC were transcribed/translated into functional luciferase enzyme using the Promega TNT system. Aliquots were withdrawn from the reaction mixture at five minute intervals and frozen on dry ice. The samples were thawed on wet ice and aliquots (0.5 μL) were mixed with luciferin assay reagent (10 μL; Promega). Light emission from the assay was quantified in a scintillation counter. Light emission (sqrt (cpm—background)) was converted to luciferase concentration by comparison to a standard curve and plotted vs. time. As shown in FIG. 10, active luciferase was produced by normal and boronated templates at the same rate.

EXAMPLE 9

Resistance of Boronated DNA to Digestion by 5' Exonuclease

Normal and boronated PCR products were prepared as described in Example 6 (Taq only; primers: phi9for, phi9rev (see Example 6); Taq buffer; dNTPs: 100 micromolar, Taq: 5 units; T7 DNA: 5 ng; 25 cycles: 95 degrees C. (15 min), 60 degrees C. (1 min), 72 degrees C. (1 min), and repeat) except that, for base-specific boronated samples, dNT$^b$P's of the second-eluting (HPLC) diastereoisomer (50 μM) were added to the reaction. After amplification, the samples were supplemented with MgCl$_2$ (2.5 mM) and DTT (1 mM). T7 gene 6 (25 units), a 5' exonuclease that requires a double stranded substrate, was added to an aliquot of the PCR reaction (10 μL) and allowed to react for 10 min. The samples were separated on a 1% agarose gel.

As shown in FIG. 11, normal DNA was digested to completion (compare lane 2 with lane 1). In contrast, the boronated samples were resistant to digestion (compare lanes 4, 6, 8 and 10 with lanes 3, 5, 7 and 9, respectively).

Documents referenced hereinabove are hereby incorporated in their entirety by reference.

One skilled in the art will appreciate from a reading of the foregoing disclosure that various changes in form and detail can be made without departing from the true scope of the invention.

What is claimed is:

1. A method of sequencing a nucleic acid comprising:
   i) A) enzymatically amplifying said nucleic acid in the presence of (a) nucleotides required to effect said amplification, which nucleotides, once incorporated into a product of said amplification, are susceptable to enzymatic degradation by an exonuclease specific for one end of said product of said amplification, and (b) an α-P-borano-substituted nucleotide that is selectively incorporated into said product of said amplification in lieu of one of said nucleotides of (a), which α-P-borano-substituted nucleotide, once incorporated into said product of said amplification, is resistant to enzymatic degradation by said exonuclease, and
   B) repeating said enzymatic amplification, each repeat being carried out in the presence of a α-P-substituted nucleotide, each of which α-P-borano-substituted nucleotides is selectively incorporated into said product of said amplification in lieu of a different one of said nucleotides of (a), each of said third and fourth modified α-P-borano-substituted nucleotides being resistant to enzymatic degradation by said exonuclease once incorporated into said product of said amplification;
   ii) treating the products of said amplification of step (i) with said exonuclease so that digestion fragments are produced terminating at the sites of incorporation of said α-P-borano-substituted nucleotides;
   iii) separating the fragments resulting from the treatment of step (ii) and detecting the position of each of said α-P-borano-substituted nucleotides in the products of said amplification.

2. The method according to claim 1 wherein said amplification is effected by polymerase chain reaction.

3. The method according to claim 1 wherein said treatment of step (ii) is effected using exonuclease III.

4. The method according to claim 1 wherein said separation of step (iii) is effected by gel electrophoresis.

5. The method according to claim 1 wherein said α-P-borano-substituted nucleotides are 2'-deoxynucleoside 5'-α-borano-triphosphates.

6. The method according to claim 1 wherein said treatment of step (ii) is effected using a 3' to 5' exonuclease.

7. A method of sequencing a nucleic acid comprising:
   i) A) enzymatically amplifying said nucleic acid in the presence of (a) nucleotides required to effect said amplification, which nucleotides, once incorporated into a product of said amplification, are susceptable to enzymatic degradation by an exonuclease specific for one end of said product of said amplification, and (b) an α-P-borano-substituted nucleotide that is selectively incorporated into said product of said amplification in lieu of one of said nucleotides of (a), which α-P-borano-substituted nucleotide, once incorporated into said product of said amplification, is resistant to enzymatic degradation by said exonuclease, and
   B) repeating said enzymatic amplification, each repeat being carried out in the presence of a α-P-borano-substituted nucleotide, each of which α-P-borano-substituted nucleotides is selectively incorporated into said product of said amplification in lieu of a different one of said nucleotides of (a), each of said α-P-borano-substituted nucleotides being resistant to enzymatic degradation by said exonuclease once incorporated into said product of said amplification;
   ii) degrading, by using an exonuclease, the products of said amplification of step (i) containing said α-P-borano-substituted nucleotides from one end thereof so that resulting fragment patterns reveal the position of each of said α-P-borano-substituted nucleotides in the products of said amplification.

8. The method according to claim 7 wherein said exonuclease is a 3'exonuclease.

9. The method according to claim 7 wherein said exonuclease is a 5'exonuclease.

10. The method according to claim 7 wherein said products of step (i) are fragmented prior to step (ii).

11. The method according to claim 7 wherein said products of step (i) are greater than 1 kilobase in length.

12. The method according to claim 7 wherein said amplification is effected by polymerase chain reaction.

13. The method according to claim 7 wherein said α-P-borano-substituted nucleotide is a 2'deoxynucleoside 5'-α-borano-triphosphate.

14. A method of bidirectionally sequencing a double-stranded nucleic acid comprising:
   i) enzymatically amplifying each strand of said nucleic acid in the presence of (a) nucleotides required to effect said amplification, which nucleotides, once incorporated into a product of said amplification, are susceptible to enzymatic degradation by an exonuclease specific for one end of said product of said amplification, and (b) an α-P-borano-substituted nucleotide that is selectively incorporated into said product of said amplification in lieu of one of said nucleotides of (a), which α-P-borano-substituted nucleotide, once incorporated into said product of said amplification, is resistant to enzymatic degradation by said exonuclease, and repeating said enzymatic amplification, each repeat being carried out in the presence of a α-P-borano-substituted nucleotide, each of which α-P-borano-substituted nucleotides is selectively incorporated into said product of said amplification in lieu of a different one of said nucleotides of (a), each of said α-P-borano-substituted nucleotides being resistant to enzymatic degradation by said exonuclease once incorporated into said product of said amplification;

wherein said enzymatic amplification is effected using a first primer complementary to a first strand of said nucleic acid, said first primer being linked at the 5' end thereof to a first member of a binding pair, and a second primer complementary to a second strand of said nucleic acid, ii) contacting the products of said step (i) with a solid support having a second member of said binding pair linked thereto and under conditions such that products of said step (i) either linked to said first member of said binding pair or hybridized to products of step (i) linked to said first member of said binding pair, complex with said second member of said binding pair bound to said solid support;

iii) digesting the complex resulting from step (ii) with an exonuclease specific for one end of said products of said amplification, said digestions terminating at the sites of incorporation of said α-P-borano-substituted nucleotides;

iv) denaturing the digests resulting from step (iii);

v) separating fragments resulting from the denaturation of step (iv) and detecting the position of each of said α-P-borano-substituted nucleotides in the products of said amplification.

15. The method according to claim 14 wherein said wherein said α-P-borano-substituted nucleotide is a 2'-deoxynucleoside 5'-α-borano-triphosphate.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 509 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---|
| GGAGCGTAGG | AAATAATACG | ACTCACTATA | GGGAGAGGCG | AAATAATCTT | CTCCCTGTAG | 60
| TCTCTTAGAT | TTACTTTAAG | GAGGTCAAAT | GGCTAACGTA | ATTAAAACCG | TTTTGACTTA | 120
| CCAGTTAGAT | GGCTCCAATC | GTGATTTTAA | TATCCCGTTT | GAGTATCTAG | CCCGTAAGTT | 180
| CGTAGTGGTA | ACTCTTATTG | GTGTAGACCG | AAAGGTCCTT | ACGATTAATA | CAGACTATCG | 240
| CTTTGCTACA | CGTACTACTA | TCTCTCTGAC | AAAGGCTTGG | GGTCCAGCCG | ATGGCTACAC | 300
| GACCATCGAG | TTACGTCGAG | TAACCTCCAC | TACCGACCGA | TTGGTTGACT | TTACGGATGG | 360
| TTCAATCCTC | CGCGCGTATG | ACCTTAACGT | CGCTCAGATT | CAAACGATGC | ACGTAGCGGA | 420
| AGAGGCCCGT | GACCTCACTA | CGGATACTAT | CGGTGTCAAT | AACGATGGTC | ACTTGGATGC | 480
| TCGTGGTCGT | CGAATTGTGA | ACCTAGCGA | | | | 509

( 2 ) INFORMATION FOR SEQ ID NO:2:

( i ) SEQUENCE CHARACTERISTICS:
        ( A ) LENGTH: 629 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| ACAGCTTCAC | CTGAGGCTAT | GGCTGCTGCC | GCTGATTCCG | TAGGTTTACA | GCCGGGAATT | 60
| TAATACGACT | CACTATAGGG | AGACCTCATC | TTTGAAATGA | GCGATGACAA | GAGGTTGGAG | 120
| TCCTCGGTCT | TCCTGTAGTT | CAACTTTAAG | GAGACAATAA | TAATGGCTGA | ATCTAATGCA | 180
| GACGTATATG | CATCTTTTGG | CGTGAACTCC | GCTGTGATGT | CTGGTGGTTC | CGTTGAGGAA | 240
| CATGAGCAGA | ACATGCTGGC | TCTTGATGTT | GCTGCCCGTG | ATGGCGATGA | TGCAATCGAG | 300
| TTAGCGTCAG | ACGAAGTGGA | AACAGAACGT | GACCTGTATG | ACAACTCTGA | CCCGTTCGGT | 360
| CAAGAGGATG | ACGAAGGCCG | CATTCAGGTT | CGTATCGGTG | ATGGCTCTGA | GCCGACCGAT | 420
| GTGGACACTG | GAGAAGAAGG | CGTTGAGGGC | ACCGAAGGTT | CCGAAGAGTT | TACCCCACTG | 480
| GGCGAGACTC | CAGAAGAACT | GGTAGCTGCC | TCTGAGCAAC | TTGGTGAGCA | CGAAGAGGGC | 540
| TTCCAAGAGA | TGATTAACAT | TGCTGCTGAG | CGTGGCATGA | GTGTCGAGAC | CATTGAGGCT | 600
| ATCCAGCGTG | AGTACGAGGA | GAACGAAGA | | | | 629

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAGGAACAGC TATGGCCTCA                                                          20

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTGTAGCTGA GGCCATAGCT GTTCCTG                                                    27

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

TATCGGCCTC AGGAAGATCG                                                            20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

TCACACAGGA AACACTATGC                                                            20

( 2 ) INFORMATION FOR SEQ ID NO:7:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

GGAGCGTAGG AAATAATAC                                                             19

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:8:

CGGTTTTAAT TACGTTAGCC                                                            20

( 2 ) INFORMATION FOR SEQ ID NO:9:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:9:

CAGGAACAGC TATGGCCTC                                                             19

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
ACAGCTTCAC CTGAGGCTAT GG                                                22
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
TCTTCGTTCT CCTCGTACTC ACGC                                              24
```

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TTGATGGAGC TGATACCGCT CG                                                22
```

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
ATCTTCCCCA TCGGTGATGT CG                                                22
```

( 2 ) INFORMATION FOR SEQ ID NO:14:

( i ) SEQUENCE CHARACTERISTICS:
        ( A ) LENGTH: 190 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GTGAGGTCGG TCGAAAGGCC GTGGCGAAGA CCACGGCCTT TGGTCCGTTT CGCGGTAAGC        60
GGTAAGTCCG ATGCGTTGAC AACCCTTCCC GCTAGCCACG CCCGGAGAAG CGATAATGCG       120
```

```
GTCGACCGCT  TTCCCCCTAC  ACGACGTTCC  GCTAATTCAA  CCCATTGCGG  TCCCAAAAGG      180

GAAAGGGTC                                                                   190
```